United States Patent [19]

Harjes et al.

[11] 3,974,032
[45] Aug. 10, 1976

[54] LOW D.E. STARCH HYDROLYSATES OF IMPROVED STABILITY PREPARED BY ENZYMATIC HYDROLYSIS OF DEXTRINS

[75] Inventors: Clarence F. Harjes, Hinsdale; Harry W. Leach, Chicago; John M. Trp, Argo, all of Ill.

[73] Assignee: CPC International Inc., Englewood Cliffs, N.J.

[22] Filed: Mar. 5, 1973

[21] Appl. No.: 337,796

[52] U.S. Cl.............................. 195/31 R; 426/48; 426/658; 426/661
[51] Int. Cl.$^2$......................................... C12D 13/02
[58] Field of Search........... 195/31 R; 426/658, 661, 426/48; 127/38, 54, 29

[56] References Cited
UNITED STATES PATENTS

| | | | |
|---|---|---|---|
| 3,484,287 | 12/1969 | Vonk .................................... | 127/38 |
| 3,756,853 | 9/1973 | Meyer et al............................ | 127/38 |
| 3,756,919 | 9/1973 | Deaton et al. ..................... | 195/31 R |

OTHER PUBLICATIONS

Whistler et al. *Starch Chemistry and Technology* vol. II Academic Press New York, London (1967) pp. 226–276.

Brimhall et al., *Industrial and Engineering Chemistry*, vol. 36, (1944), pp. 72–75.

*Primary Examiner*—A. Louis Monacell
*Assistant Examiner*—Thomas G. Wiseman
*Attorney, Agent, or Firm*—Albert P. Halluin; Donald G. Marion

[57] ABSTRACT

A low D.E. starch hydrolysate having a D.E. not substantially above about 20, a relatively narrow molecular weight distribution such that its weight average molecular weight to its number average molecular weight ratio of $\overline{M}w/\overline{M}n$ is less than about 20 and said hydrolysate being further characterized as containing less than about 20% by weight, dry basis, of starch oligosaccharides having a degree of polymerization greater than about 200. The low D.E. starch hydrolysates are prepared by enzymatically hydrolyzing starch dextrins having a degree of branching of at least about 7%. The low D.E. starch hydrolysates are resistant to the formation of haze at high solids and they exhibit reduced enzyme susceptability.

18 Claims, 1 Drawing Figure

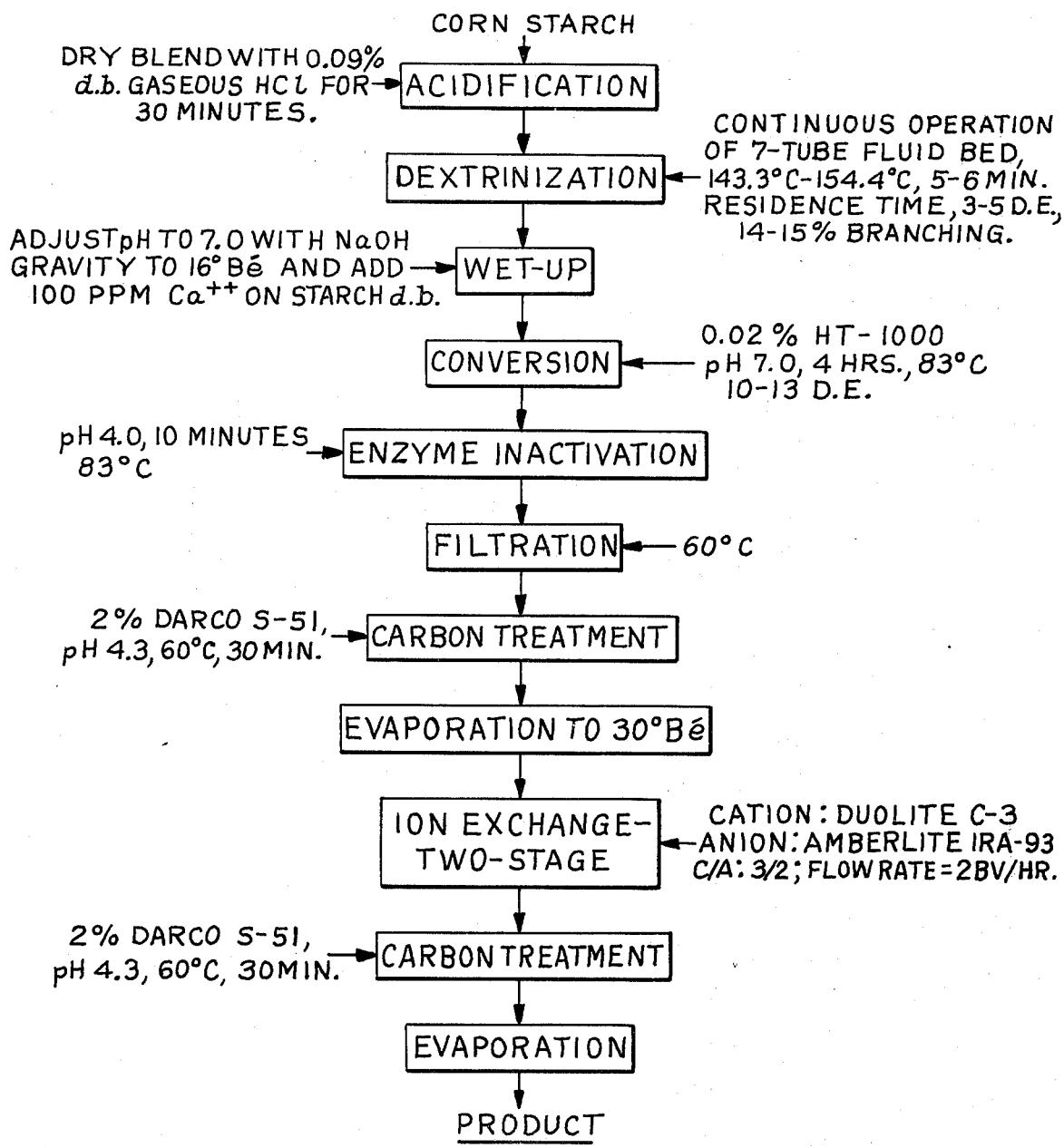
FLOW DIAGRAM FOR PREPARATION OF LOW D.E. STARCH HYDROLYSATES FROM DEXTRINS.

LOW D.E. STARCH HYDROLYSATES OF IMPROVED STABILITY PREPARED BY ENZYMATIC HYDROLYSIS OF DEXTRINS

BACKGROUND OF THE INVENTION

1. Field of the Invention

This invention relates to low D.E. starch hydrolysate syrups which remain clear over a relatively long period of time at high solids concentrations. The syrups are particularly useful as extenders for synthetic sweeteners. The invention is also concerned with a method of preparing said syrups wherein the first step includes increasing the degree of branching of the starch prior to an enzymatic hydrolysis step.

2. Description Of The Prior Art

There are many processes known in the art for producing low D.E. starch hydrolysates. These processes include liquefying an aqueous slurry of starch with an acid, followed by enzymatic conversion, sometimes referred to as saccharification, or liquefying an aqueous slurry of starch with a liquefying enzyme, followed by enzymatic conversion. For example, Dutch Pat. No. 66/12486, published Apr. 3, 1967, discloses a method for hydrolyzing an aqueous slurry of starch with an acid to a D.E. of at least about 7 to no more than about 16, followed by enzymatic conversion with bacterial alpha-amylase to a D.E. in the range of from about 23 to about 35. Belgian Pat. No. 708,104, published June 18, 1968, discloses a method for hydrolyzing an aqueous slurry of starch with an acid or an enzyme to obtain a liquefied starch hydrolysate having a D.E. of less than about 15, followed by enzymatic conversion of the liquefied starch hydrolysate to a D.E. of less than about 25. It is further disclosed in said Belgian patent that exceptional results are obtained by the enzymatic liquefaction of an aqueous slurry of a waxy starch, followed by the enzymatic conversion of the liquefied waxy starch with bacterial alpha-amylase to obtain a starch hydrolysate having a D.E. in the range of from about 5 to about 25. Products produced by this latter method are extremely soluble in water and their syrups are haze resistant at low temperatures for at least three days. These products are commercially available under the trade name "Mor-Rex", sold by CPC International Inc. German Pat. No. 1,955,392, published June 16, 1971, also discloses a process for hydrolyzing an aqueous slurry of starch with an acid or an enzyme to obtain a liquefied starch hydrolysate having a D.E. of not substantially above 3, followed by enzymatic conversion with bacterial alpha-amylase to obtain a starch hydrolysate having a D.E. not substantially above 18.

The aforementioned prior art methods provide a low D.E. product which performs well in many applications, particularly when used as a carrier for synthetic sweeteners. Other applications for the low D.E. starch hydrolysates include use as a bulking or dispersing agent in synthetic creams or coffee whiteners, as a moisture-holding agent in breads, pastries, meats and as a bodying and smoothing agent in puddings, soups and frozen ice desserts.

The low D.E. starch hydrolysates of the aforementioned prior art methods are first prepared in syrup form and generally dried to a solid. However, many users of low D.E. starch hydrolysates desire a liquid product to reduce handling costs and to eliminate the need for redispersing a dried product. It has been found that one cannot store and/or ship starch hydrolysates of the desired low D.E. in highly concentrated form. To date, there is no known economical method for preparing a low D.E. syrup at high solids which is resistant to the formation of haze on storage. The low D.E. starch hydrolysates prepared by the aforementioned prior art methods tend to haze when their syrups are in concentrated form due to the association of the partially degraded starch molecules in the solution. For example, hydrolysates from corn starch having a D.E. less than about 20 when concentrated up to about 70% solids tend to quickly haze upon storage, until the point where the product sets up to a solid. Attempts to produce a low D.E. waxy starch hydrolysate product at about a 70% solids content or above and having a D.E. less than about 15 results in hazing when the syrup is stored for long periods of time, i.e., more than about three days.

Prior art methods for preparing low D.E. starch hydrolysates using the enzyme bacterial alpha-amylase generally have required an additional liquefaction step with either an acid or an enzyme to provide an aqueous dispersion substantially free of residual starch granules. This technique has been considered necessary in order to provide a uniform conversion of the aqueous starch dispersion with the hydrolyzing enzyme. Heretofore, it has been believed that this aqueous liquefaction step has been necessary to prevent the occurrance of very large starch molecules in the low D.E. starch hydrolysate product. The presence of these large starch molecules is objectionable from the standpoint of filtration and retrogradation, the latter of which is associated with haze formation in the low D.E. syrups.

Heretofore, it has been believed that dextrins would not be a suitable starting material for preparing low D.E. starch hydrolysates by conversion of the same with bacterial alpha-amylase. The reason for this belief is because the conditions used in the art to manufacture dextrins result in a bond rearrangement which causes branching to occur, and because of this bond rearrangement, the dextrins are not expected to undergo a significant conversion in order to obtain a starch hydrolysate which will be readily soluble in water.

SUMMARY OF THE INVENTION

The present invention provides a low D.E. starch hydrolysate having a D.E. not substantially above about 20, a relatively narrow molecular weight distribution such that its weight average molecular weight to number average molecular weight ratio of $\overline{M}w/\overline{M}n$ is less than about 20, and being further characterized as containing less than about 20% by weight, dry basis, of starch oligosaccharides having a degree of polymerization greater than about 200 ($DP_{200+}$). The novel low D.E. starch hydrolysates of the present invention are further characterized as producing a fluid solution resistant to the formation of haze and having reduced enzyme susceptability. The starch hydrolysates are capable of being dissolved in water to a solids content of at least 50% by weight to obtain syrups which exhibit remarkable solution stability and remain haze-free over relatively long periods of time, compared to the prior art low D.E. starch hydrolysate syrups. Thus, the syrups of the present invention may be stored and shipped in highly concentrated form without fear of hazing occurring as a minimum detriment or without the danger of the syrup setting up to a solid or semi-solid state.

The low D.E. starch hydrolysates of the present invention can be used to make syrups having a solids content of 50–80%, more often 50–75% by weight, and most generally 65–73% by weight.

Although the low D.E. starch hydrolysates of the present invention find great utility in the form of concentrated syrups, these syrups may also be spray dried and later reconstituted to a highly concentrated syrup which is resistant to the formation of haze.

The present invention is also concerned with a method of preparing the just described starch hydrolysates by the enzymatic conversion of a starch dextrin with bacterial alpha-amylase. More specifically, the low D.E. starch hydrolysates of improved stability are prepared by a process comprising treating a starch dextrin having a degree of branching of at least about 7% with a bacterial alpha-amylase enzyme preparation to achieve a hydrolysate product having a D.E. not substantially above about 20, a relatively narrow molecular weight distribution such that its weight average molecular weight to number average molecular weight ratio of $\overline{M}w/\overline{M}n$ is less than about 20, and being further characterized as containing less than about 20% by weight, dry basis, of starch oligosaccharides having a degree of polymerization greater than about 200.

It is essential that the degree of branching of the starch dextrin be at least about 7% in order to provide a low D.E. starch hydrolysate of improved stability and the proper molecular weight distribution and carbohydrate characteristics alluded to hereinabove. Preferably, the starch dextrin is treated by mixing it with water to a solids content of less than about 50% by weight and thereafter hydrolyically treating it with a suitable enzyme such as bacterial alpha-amylase. After a starch hydrolysate is obtained having a D.E. not substantially above about 20, the conversion action of the enzyme is terminated. The starch hydrolysate may then be concentrated to the desired solids content, preferably greater than about 50% by weight, dry basis, and more preferably, to a solids content in the range of from about 50–80% by weight, dry solids.

BRIEF DESCRIPTION OF THE DRAWING

For a more complete understanding of the nature and scope of the invention, reference may now be had to the following detailed description thereof, taken in connection with the accompanying drawing, wherein:

There is a flow diagram illustrating the preferred method for preparing the low D.E. starch hydrolysates of the present invention.

DESCRIPTION OF THE PREFERRED EMBODIMENTS

The low D.E. starch hydrolysates of the invention exhibit excellent solution stability and remain non-hazing over remarkable periods of time, even when they are highly concentrated. It is postulated that the improved solution stability of the low D.E. starch hydrolysates of the invention is due to their relatively narrow molecular weight distribution and the fact that less than about 20% by weight, dry basis, of their starch oligosaccharides having a degree of polymerization greater than about 200, exists in the low D.E. starch hydrolysates.

The low D.E. starch hydrolysates of the invention normally have a D.E. not substantially above about 20, and preferably a D.E. in the range of from about 5 to about 16. A typical starch hydrolysate of the invention may have a D.E. in the range of from about 9 to about 13.

The term "D.E." is used herein to refer to the reducing sugars content of the dissolved solids in a starch hydrolysate expressed as percent dextrose as measured by the Schoorl method (*Encyclopedia of Industrial Chemical Analysis*, Vol. 11, pp. 41–42).

The low D.E. starch hydrolysates of the invention have a relatively narrow molecular weight distribution. A degree of molecular weight distribution of the carbohydrate polymer is represented by a ratio of weight average molecular weight to number average molecular weight ($\overline{M}w/\overline{M}n$). The low D.E. starch hydrolysates of the present invention generally have a molecular weight distribution such that the ratio of their weight average molecular weight ($\overline{M}w$) to their number average molecular weight ($\overline{M}n$) ($\overline{M}w/\overline{M}n$) is less than about 20, and preferably less than about 17. Many of the preferred hydrolysates of the invention have a molecular weight distribution, as represented by the ratio of $\overline{M}w/\overline{M}n$, of less than about 15. Typical low D.E. starch hydrolysates of the invention have a molecular weight distribution, represented by the ratio of $\overline{M}w/\overline{M}n$, in the range of from about 6 to about 13.

The ratio of $\overline{M}w/\overline{M}n$ is also referred to in the prior art as a polydispersity factor. In any event, the molecular weight distribution represented by the ratio of $\overline{M}w/\overline{M}n$ or the polydispersity factor of the hydrolysates of the invention is generally less than about 20.

As pointed out hereinabove, the term "polydispersity" (PD) is defined as the ratio of the weight average molecular weight ($\overline{M}w$) to number average molecular weight ($\overline{M}n$). This term indicates how broad or narrow the molecular weight distribtution is in any given sample. That is, the greater the numerical value, the broader the molecular weight distribution. The molecular weight distribution or polydispersity factor of the prior art low D.E. starch hydrolysates, i.e., those starch hydrolysates prepared by the methods described in Belgian Pat. No. 708,104 and German Pat. Publication No. 1,955,392 generally have a value greater than about 35, indicating that these low D.E. starch hydrolysates have a rather broad molecular weight distribution. Thus, the low D.E. starch hydrolysates of the present invention have a much narrower molecular weight distribution than the prior art low D.E. starch hydrolysates.

The number average molecular weight can be determined by any of the following methods:

1. Calculation from D.E. and dextrose analysis in accordance with the following equation:

$$\overline{M}n = \frac{20,500}{D.E. + (0.1388)(\text{dextrose, \% d.b.})}; \text{ and}$$

2. Gel permeation chromatography (GPC) using dimethylformamide (DMF) as a solvent.

It has been found that the foregoing two methods for estimating number average molecular weight give values which are in good agreement. The weight average molecular weights of the starch hydrolysates can also be determined by gel permeation chromatography using available standards.

Another unique characteristic of the low D.E. starch hydrolysates of the invention is the relatively low amount of starch oligosaccharides having a degree of polymerization greater than about 200, i.e., the amount of starch oligosaccharides having more than 200 repeating anhydroglucose units per molecule ($DP_{200+}$).

The low D.E. starch hydrolysates of the present invention generally have less than 20% by weight, dry basis, of starch oligosaccharides having a degree of polymerization greater than 200, and preferably the starch hydrolysates will have less than about 15% by weight, dry basis, of starch oligosaccharides having a degree of polymerization greater than 200. A typical starch hydrolysate of the present invention may have only 8% to about 12% by weight, dry basis, of starch oligosaccharides having a degree of polymerization greater than about 200. Typical prior art starch hydrolysates having a low D.E. such as those prepared from waxy starch as disclosed in Belgian Pat. No. 708,104, have more than 35% by weight, dry basis, of starch oligosaccharides having a degree of polymerization greater than about 200.

Thus, it can be seen from the above that the low D.E. starch hydrolysates of the present invention contain a very small amount of high molecular weight starch oligosaccharides, as well as a very small amount of carbohydrates which contribute to increasing the D.E. of the starch hydrolysates. Moreover, the starch hydrolysates of the present invention have a relatively narrow molecular weight distribution. These unique characteristics in combination with one another provide a product which is extremely stable as a solution at high solids and, therefore, represents a marked advance in the art of low D.E. starch hydrolysates.

The low D.E. starch hydrolysates of the present invention are also characterized as having a descriptive ratio of at least about 2. The description ratio is defined as being the quotient obtained by dividing the sum of the percentage of saccharides, dry basis, having a degree of polymerization of 1 to 6, by the D.E. This is a characteristic common to the prior art low D.E. starch hydrolysates referred to in the above-cited patents. Thus, the low D.E. starch hydrolysates of the present invention enjoy the beneficial characteristics of the prior art low D.E. starch hydrolysates, i.e., they have a low D.E. and a descriptive ratio of at least about 2, in addition to a unique narrow molecular weight distribution and minimum starch oligosaccharide content having a degree of polymerization greater than about 200. The combination of these characteristics in the starch hydrolysates of the present invention permit the starch hydrolysates to be non-hygroscopic and completely soluble in cold water, as well as being resistant to the formation of haze at high solids concentration for long periods of time. Typically, the low D.E. starch hydrolysates of the present invention remain haze-free at solids concentrations of more than 70% by weight, dry basis, for a period of more than 90 days when their D.E. is in the range from about 9 to about 13.

The Starch Dextrins

The unique low D.E. starch hydrolysates of the invention are conveniently prepared by the enzymatic conversion of a starch dextrin. The starch dextrin may be derived from any suitable source, providing it has a degree of branching of at least about 7%. As it is well-known, untreated starch generally has a degree of branching of about 3.6%. It is important to the success of the present invention that the starting material, i.e., the starch dextrin, has a degree of branching of at least about 7%. The degree of branching of the starch dextrin necessary to obtain the unique low D.E. starch hydrolysates of the invention is generally inversely proportional to the D.E. of the final product. In other words, in order to obtain improved stability of the final low D.E. starch hydrolysate of a 5 D.E. product, a higher degree of branching is necessary than a starch hydrolysate having a D.E. of about 16. The starch dextrins useful in the practice of the present invention will generally have a degree of branching in the range of from about 7% to about 16%, preferably in the range of from about 9% to about 12%.

The degree of branching in a dextrin is determined by three types of analysis, i.e., dextrose equivalent value (Schoorl's D.E. discussed hereinabove), dry substance, and the amount of formic acid formed on periodate oxidation. The latter analysis, also known as formic acid value (FAV) expressed as milliequivalents of formic acid per gram dry substance, is determined by low temperature oxidaion (2°C) with sodium metaperiodate under rigidly controlled conditions. This method is more fully described by R. W. Kerr and F. C. Cleveland, *J. Am. Chem. Soc.*, 74, 4036–4039 (1952) and by the same authors in *Die Stärke*, 5, 261–266 (1953) the disclosures of which are incorporated herein by reference.

Periodate oxidation produces one molecule of formic acid from each non-reducing terminal glucose unit and two molecules of formic acid from each reducing terminal glucose unit. Thus, changes in the FAV when calculated on a mole basis indicate degree of branching in dextrin. From the foregoing three analyses, the degree of branching is calculated as follows:

1. Calculate number average molecular weight ($\overline{M}n$):

$$\overline{M}n = 20{,}500/D.E.$$

Note: Correction of D.E. for dextrose in dextrin is disregarded because the amount of dextrose present in dextrins is negligible.

2. Convert formic acid value (FAV) from milliequivlents per g.d.s. to equivalents per mole:

$$FAV, \text{ eq/mole} = FAV, \text{ meq/g.d.s.} \times \overline{M}n/1{,}000$$

3. Calculate number of branches per mole:

$$\text{Branches/mole} = (FAV, \text{ eq/mole} - 3)/1$$

Note: Periodate oxidation produces one formic acid molecule from each non-reducing end group and two molecules of formic acid from each reducing end group.

4. Calculate total linkages per mole:

$$\text{Linkages/mole} = (\overline{M}n - 18/162 - 1$$

5. Calculate degree of branching:

$$\text{Branching, \%} = (\text{Branches/mole})/(\text{Linkages/mole}) \times 100$$

The process of the present invention contemplates the use of any starch dextrin, providing it has the appropriate degree of branching as alluded to hereinabove. For example, suitable dextrins as starting materials in the process of the invention include the commercially available canary potato dextrins, canary tapioca dextrins (the latter two manufactured and sold by Stein-Hall and Company), and the canary dextrins manufactured and sold by CPC International Inc., such as the GLOBE dextrins and Excello dextrins. Commercially available white dextrins may also be employed as the starch dexrin in the process of the present invention. The canary dextrins are, of course, more extensively dextrinized, whereas the white dextrins are the result of less rigorous reactions. In the usual procedure of heating the starch in its natural dry stte, the temperature is generally maintained within the same range to produce both white and canary dextrins. To produce the white dextrins, the starch is not acid-heated for as long a time or, alternatively, less acid is employed.

As it is well-known, dextrins are the products of partial hydrolysis obtained by heating starch in its natural dry state. Normally, the starch contains from about 10% to about 12% by weight moisture during the initial stage of dextrinization. During the dry heating of the naturally dry starch, the natural moisture in the starch is removed, whereupon dextrinization and branching commences. During the dextrinization reaction, both hydrolysis and condensation is effected. Branching occurs as a result of repolymerization of the partially hydrolyzed starch dextrin when the moixture in the starch is below about 3% by weight. Thus, when the starch drys, branching begins.

The formula for starch dextrin can be written $(C_6H_{10}O_5)_n$, where n is a variable (rather than a mathematical constant) and smaller than the value for $n$ in starch. As pointed out above, dextrins are obtained in several different grades by heating starch for varying lengths of time at temperatures ranging up to about 240°C. The amylodextrin, erythrodextrin, achrodextrin, and so forth, produced by this means may be graded roughly as to molecular size by the standard iodine test.

The dextrinization reaction can be catalyzed by treating the naturally dry starch with an acid either before or during the heating of the starch. Any acid may be utilized for this purpose, such as sulfuric acid, sulfurous acid, hydrochloric acid, and the like. Preferably, aqueous dilute hydrochloric acid or anhydrous hydrogen chloride gas is sprayed onto the starch particles before or during the heating process. Other chemicals, such as Borax, may also be incorporated into the starch during the dextrinization process.

The initial starch which is employed to prepare the starch dextrins utilized in the process of the present invention may be derived from a wide variety of starchy materials, such as cereal starches, waxy starches, and/or root starches. Typical of these groups are the non-waxy cereal starches, such as corn starch and wheat starch; potato starch; tapioca starch; grain sorghum starch; rice starch; waxy starches such as waxy milo starch and waxy maize starch; and the like. The non-waxy starches are the preferred starches, corn starch being particularly preferred. The term "starch hydrolysate" as used herein encompasses hydrolyzed starch materials derived from a wide variety of starch sources known in the industry.

In addition, cereal grits such as corn grits, may be used in the starting materials, such as those containing up to about 9% by weight protein. Thus, grits produced from dry milling such as hominy grits, Brewers' grits, corn meal or flours may be employed as the starting material.

The prior art is replete with methods for preparing partially soluble dextrins from starch by dilute acid hydrolysis, enzyme action or dry heating. These dextrins may be prepared in a fluidized bed such as the method described in U.S. Pat. Nos. 2,845,368, 3,003,894 and 3,320,074, or by the method alluded to in British Pat. Specification No. 801,524. Generally speaking, dextrins have a D.E. less than about 7, and more specifically, a D.E. of less than 3. Depending on the manner in which the dextrin is prepared, the dextrins vary in their solubility in water. However, most dextrins are relatively insoluble in solutions at high solids.

One of the preferred embodiments of the invention is to provide a process whereby naturally dry starch is heated with or without a catalyst in a fluidized bed such as that disclosed in U.S. Pat. No. 2,854,368, the disclosure of which is incorporated herein by reference. The starch is treated in such a manner to achieve the proper degree of branching, whereupon the starch dextrin is cooled, neutralized and treated as an aqueous slurry with a hydrolytic enzyme, e.g., a bacterial alpha-amylase enzyme preparation.

The fluidized bed technique used to prepare the starch dextrins is preferably performed by suspending the starch in a suitable vessel by means of passing a gas upwardly therethrough at appropriate velocity whereby the starch material resembles, in appearance, for many purposes a true fluid or liquid. The starch material subjected to the fluidized bed dextrinization may be treated with a catalyst such as an acid either before or during the fluidized bed treatment.

The fluidized bed may be operated at a wide range of temperatures, to effect dextrinization and branching of the starch. Generally speaking, the fluidized bed reactor is operated in a manner such that the starch is heated at a temperature in the range of from about 65°C to about 210°C, preferably in the range of from about 100°C to about 180°C. A temperature in the range of from about 120°C to about 165°C is particularly preferred.

The suspending gas medium employed to maintain the starch in a fluidized condition may include any inert gas or a gas containing materials which will catalyze the dextrinization reaction. Suitable gases include dry air, steam, argon, nitrogen, carbon dioxide, flue gas, chlorine, and the like. Preferably, dry air or steam are used to fluidize the starch in the fluidized bed reactor vessel.

A preferred method for preparing the starch dextrin in the fluidized bed is to first treat the starch with an acid. For example, a weighed amount of acid is sprayed on a bed of starch while continuously blending the starch to provide a homogeneous acidified starch mixture. The use of a ribbon blender has been found to be particularly suited for uniformly blending the acid on the starch. As pointed out above, any suitable acid may be employed. However, best results are obtained by using anhydrous hydrogen chloride gas. After the starch has been acidified, it is placed in the fluid bed reactor vessel to be dextrinized. However, best results are obtained by flash drying the starch to a moisture content of about 8% by weight prior to charging the starch into the fluidized bed reactor vessel.

The blended and treated starch is suitably charged into an agititated fluid bed which has been preheated to the desired temperature. The starch is preferably charged through the top of the fluid bed reactor vessel while continuously agitating the starch. The starch is fluidized by maintaining an upward flow of gas through the bed of starch by introducing the gas from beneath the bed. The gas is withdrawn from a suitable outlet above the top of the bed. Of course, the upward velocity of the gas flow should be sufficient to suspend and vigorously agitate the starch particles within the bed, but insufficient to convey a substantial portion of the starch out through the open outlet. If desired, the effluent gas withdrawn from the top of the fluidized bed reactor vessel may be recycled. The water vapor entrained in the effluent gas derived from the starch may be condensed or recycled, as is.

A preferred reactor vessel comprises one or more tubes suitably heated by pressurized steam jackets surrounding the tubes. The reactor vessel can also be equipped with means for recovering the starch dextrin whereby the starch is continuously agitated to avoid the formation of lumps. Also, the reactor vessel can be equipped with means for cooling and/or neutralizing the starch dextrin. For example, once the desired degree of branching in the starch dextrin has been achieved, the reaction is stopped by rapidly cooling and/or neutralizing the starch dextrin. Suitable cooling temperatures for terminating the dextrinization reaction are in the range of from about 50°C to about 135°C. If desired, means for applying or spraying neutralizing agents such as ammonia, ammonium carbonate or ammonium bicarbonate can be suitably provided to further prepare the starch dextrin for the subsequent treatment with the hydrolytic enzyme and to terminate the dextrinization reaction.

Enzymatic Conversion Of Starch Dextrin

The enzymatic conversion step (also referred to as enzymatic saccharification, dextrinization, liquefaction or hydrolysis of the starch) is accomplished by treating an aqueous slurry of the above-described starch dextrins with a hydrolytic enzyme preparation such as alpha-amylase, particularly a bacterial alpha-amylase preparation, to achieve a starch hydrolysate having a D.E. not substantially above 20. The starch dextrin is first dispersed or solubilized in water at a relatively high solids concentration, i.e., up to about 50% by weight prior to treatment with the enzyme. Preferably, the solids content of the starch dextrin slurry will be in the range of between 20% and 40% by weight, i.e., about 10° to about 20° Baume.

A particularly preferred embodiment of the process comprises heating the dextrinized starch in an autoclave (i.e., at a temperature above about 100°C and at a pressure of about 15 psig) prior to treatment with the enzyme. Best results are obtained by autoclaving the starch dextrin at an acidic pH, i.e., a pH of less than 3. The autoclaving of the starch dextrin improved the filtration and refining of the final product. However, it sometimes tends to increase the color of the product.

The pH of the starch dextrin slurry is preferably adjusted to a pH from about 6 to about 9 and, more preferably, from about 6.5 to about 7.5 to provide optimum conditions for enzymatic activity during hydrolytic conversion reaction.

The enzymatic hydrolytic and conversion reaction is conducted at a temperature in the range of from about 60°C to about 85°C, preferably a temperature in the range of from about 70°C to about 80°C for a time sufficient to produce a hydrolysate product having the desired D.E. value, preferably a value not substantially above about 20 and, more preferably, a value between 9 and 16.

The preferred hydrolytic enzyme used for the conversion of the starch dextrin to low D.E. starch hydrolysates is a bacterial alpha-amylase. This is a starch liquefying, heat resistant hydrolytic alpha-amylase. Suitable bacterial alpha-amylase preparatins may be produced by certain strains of *Bacillus subtilis, Bacillus mesentericus*, and the like, by conventional fermentation methods. Suitable commercially available bacterial alpha-emylase preparations include Takamine "HT-1000", the proprietary name of a bacterial alpha-amylase preparation which also contains about 21% by weight calcium, as is, which is produced and marketed by Miles Chemical Laboratory, "Rhozyme H-39" manufactured and sold by Rohm and Haas, "CPR-8" and "W" enzyme manufactured and sold by the Wallerstein Division of Baxter Laboratories, Inc., "Thermamyl" produced by Novo Industri A/S, Copenhagen, Denmark, and distributed by Enzyme Development Corporation, a division of Biddle Sawyer Corp. and other commercially available bacterial alpha-amylases.

The quantity of bacterial alpha-amylase preparation required for obtaining the desired starch hydrolysate will be dependent upon the activity of the bacterial alpha-amylase preparation, the conversion temperature of the conversion medium, the pH of the medium and the desired terminal D.E. Suitable conditions are easily selected. For example, a bacterial alpha-amylase preparation having an activity substantially equivalent to the "HT-1000" product of Miles Chemical Laboratory would be used in an amount between about 0.005% and about 0.5% by weight of the starch dextrin, dry basis, and preferably an amount between about 0.01% and 0.3% by weight, dry basis. The conversion conditions would include a temperature of about 80°C and a pH of about 7 for a period of time sufficient to attain the desired D.E. The time of treatment will depend, of course, upon the enzyme dosage. Normally, the treatment time will range from about 1 to about 18 hours. Various materials may be added to the enzyme preparation or to the starch dextrin slurry to enhance the activity of the enzyme or stabilize the enzyme. For example, calcium compounds may be added to improve the heat stability of the enzyme.

When the desired D.E. of the starch hydrolysate is obtained in the enzyme conversion step, the hydrolysate liquor is subjected to a treatment to inactivate residual enzyme. The particular treatment utilized is not critical and any conventional treatment for inactivating the particular enzyme present is suitable for use. For alpha-amylases, such methods usually involve a suitable shift of the pH, i.e., a pH of 4 or less, a heat treatment at elevated temperatures such as above 100°C, or both.

After termination of the enzymatic conversion, the low D.E. starch hydrolysate may be refined and concentrated to the concentration levels set forth hereinabove, or spray dried to solid products. The starch hydrolysate may be used in unaltered form, but is commonly conventionally refined by treatment with vegetable carbon, ion exchange resins, filtration, centrifugation, and the like.

As it can be seen from the above, a preferred embodiment of the process for producing low D.E. starch hydrolysates comprises:

a. dextrinizing starch by introducing a bed of starch powder into a vessel, maintaining an upward flow of gas through said bed by introducing the gas from beneath said bed and withdrawing it from an outlet above the top of said bed, the upward velocity of said gas flow being sufficient to suspend and vigorously agitate the starch particles within said bed but insufficient to convey a substantial portion of the starch out through said upward outlet, heating said bed of starch in said agitated condition to dextrinizing temperature and maintaining said dextrinizing temperature until said starch has degree of branching of at least about 7%.

b. cooling said bed of agitated starch and withdrawing said starch dextrin from said vessel, c. subjecting a mixture of said dextrinized starch and water at a solids content of less than about 50% by weight dry basis to the hydrolytic action of bacterial alpha-amylase to achieve a hydrolysate product having a D.E. not substantially above about 20, d. stopping the hydrolytic reaction, and e. recovering the hydrolysate so produced.

The present invention having been described in detail, the following specific examples are presented to illustrate additional embodiments of the process and product thereof. It is to be understood that the examples are given for illustrative purposes only and not by way of limitation.

EXAMPLE 1

Preparation Of Low D.E. Starch Hydrolysates From Commercially Available Dextrins Aqueous dispersions of dextrins were prepared at a gravity of 14° to 18° Baume and adjusted to a pH of 6.5 by the addition of alkali. In some cases, aliquot portions of the dispersions were autoclaved at 15 psig steam pressure for 20 minutes at a temperature of 121°C prior to enzymatic conversion to improve the filtration rates. The dextrins used are commercially available canary and white dextrins manufactured and sold by CPC International Inc. under the designations indicated. The dextrins were prepared by heating dry starch catalyzed by hydrochloric acid and each of the dextrins has at least about 7% branching. The characteristics of different dextrins used as starting materials are indicated in Table I.

TABLE I

| Type Dextrin | Brand Name | Parent Starch | D.E. | Solubles |
|---|---|---|---|---|
| Canary | Excello Dextrin No. 8641 | White milo | 2.0 | 98+ |
| White | Globe Dextrin No. 7078 | Corn | 6.5 | 94 |
| White | C.P. Gum No. 7381 | Corn | 3.4 | 90 |
| White | C.P. Gum No. 7381 | Corn | 2.8 | 90+ |
| White | C.P. Gum No. 7381 | Corn | 2.4 | 90+ |

Several aliquots of dextrin dispersions were placed in conversion pots at constant temperature water baths set at 60° or 83°C and allowed to attemperate. The dextrin dispersions were dosed with sufficient bacterial alpha-amylase enzyme preparation (Takamine HT-1000), to attain the desired D.E. level in a 3–4 hour reaction period. When the desired D.E. level was attained, the enzyme was inactivated by adding an acid to lower the pH value to 4.0. The resulting low D.E. starch hydrolysates were filtered, treated with carbon and refiltered. Several of the low D.E. starch hydrolysates were evaporated to about 70% d.s., and observed for haze formation. The conditions and observations of the several enzymatic conversions of the starch dextrins are indicated in Table II.

TABLE II

| Sample No. | Type Dextrin | Code No. | D.E. | Substrate Treatment | Dispersion Be | Conv. Temp. °C | Enzyme Dosage %, HT-1000 | Conv. Time Hours | Schoorls D.E. |
|---|---|---|---|---|---|---|---|---|---|
| 1 | Canary | 8641 | 2.0 | None | 15.5 | 60 | 0.05 | 4 | 8.2 |
| 2 | White | 7078 | 6.5 | Autoclaved | 17.5 | 83 | 0.01 | 3 | 10.3 |
| 3 | White | 7078 | 6.5 | None | 15.5 | 83 | 0.02 | 4 | 11.1 |
| 4 | White | 7078 | 6.5 | Autoclaved | 17.5 | 83 | 0.02 | 4 | 12.9 |
| 5 | White | 7381 | 3.4 | Autoclaved | 17.5 | 83 | 0.02 | 3 | 8.9 |
| 6 | White | 7381 | 3.4 | None | 14.5 | 83 | 0.03 | 3.5 | 10.2 |
| 7 | White | 7381 | 3.4 | Autoclaved | 17.5 | 83 | 0.03 | 3 | 11.2 |
| 8 | White | 7381 | 2.8 | None | 16.5 | 83 | 0.03 | 3 | 11.8 |
| 9 | White | 7381 | 2.8 | Autoclaved | 16.5 | 83 | 0.03 | 3 | 12.4 |
|   |   |   |   |   | Be / d.s. |   |   |   |   |
| 10 | White | 7381 | 2.4 | None | 14.5 / 24.9 | 60 | 0.07 | 3 | 15.4 |
| 11 | White | 7381 | 2.1 | Autoclaved | 15.9 / 27.3 | 60 | 0.07 | 4 | 15.6 |
| 12 | White | 7381 | 2.4 | None | 14.5 / 24.9 | 83 | 0.07 | 3 | 16.4 |
| 13 | White | 7381 | 2.1 | Autoclaved | 15.9 / 27.3 | 83 | 0.07 | 3 | 16.1 |
| 14 | White | 7381 | 2.1 | Autoclaved | 15.9 / 27.3 | 83 | 0.07 | 4 | 17.5 |
| 15 | White | 7381 | 2.1 | Autoclaved | 15.9 / 27.3 | 83 | 0.09 | 4 | 18.3 |
| 16 | White | 7381 | 2.1 | Autoclaved | 15.9 / 27.3 | 83 | 0.15 | 3 | 19.3 |
| 17 | White | 7381 | 2.1 | Autoclaved | 15.9 / 27.3 | 83 | 0.15 | 4 | 20.0 |
| 18 | White | 7381 | 2.4 | None | 14.5 / 24.9 | 83 | 0.15 | 4 | 19.9 |

| Sample No. | % d.s. | Absorbancy 520 mμ | Absorbancy 350 mμ | Iodine Ratios | Syrup Solution Stability Observations Room Temperature Storage |
|---|---|---|---|---|---|
| 1 | 68.5 | n.d.[a] | n.d. | n.d. | Still clear after 182 days. |
| 2 | 69.4 | n.d. | n.d. | n.d. | Hazed in 6 days. |
| 3 | 69.5 | n.d. | n.d. | n.d. | Hazed in 4 weeks. |
| 4 | 70 | n.d. | n.d. | n.d. | Still clear after 133 days. |
| 5 | 70.1 | n.d. | n.d. | n.d. | Hazed in 19 days. |
| 6 | 70.4 | n.d. | n.d. | n.d. | Hazed in 14 weeks. |
| 7 | 70 | n.d. | n.d. | n.d. | Still clear after 153 days. |
| 8 | 69.9 | n.d. | n.d. | n.d. | Still clear after 112 days. |

TABLE II-continued

| | | | | | |
|---|---|---|---|---|---|
| 9 | 69.8 | n.d. | n.d. | n.d. | Still clear after after 113 days. |
| 10 | 74.4 | .111 | .847 | 7.6 | Still clear after 63 days. |
| 11 | 75.0 | .060 | .849 | 14.2 | Still clear after 62 days |
| 12 | 73.7 | .055 | .830 | 15.1 | Still clear after 62 days |
| 13 | n.d. | .056 | .859 | 15.3 | Still clear after 62 days |
| 14 | n.d. | n.d. | n.d. | n.d. | n.d. |
| 15 | n.d. | n.d. | n.d. | n.d. | n.d. |
| 16 | n.d. | n.d. | n.d. | n.d. | n.d. |
| 17 | n.d. | n.d. | n.d. | n.d. | n.d. |
| 18 | n.d. | n.d. | n.d. | n.d. | n.d. |

[a]n.d. = not determined.

It can be seen from the data set forth in Table II that the low D.E. syrups remain stable and haze-free for relatively long periods of time at very high solids concentrations. Prior art low D.E. starch hydrolysates have generally required a D.E. in excess of 16 to remain haze-free for more than 2–3 days at a solids concentration of about 70% or more. This is particularly true for low D.E. syrups produced from corn starch. However, the low D.E. starch hydrolysate syrups produced from dextrins remain stable well in excess of 3 days at a solids content of about 70%, even when the D.E. is about 10. This is quite unexpected since most of the syrups evaluated are derived from corn starch. The syrup samples which did not undergo significant enzymatic conversion (i.e., increase in D.E. by the action of bacterial alpha-amylase) tended to haze earlier than other syrups. For example, in Sample No. 2, the D.E. was only increased from 6.5 to 10.3 and in Sample No. 5, the D.E. was only increased from 3.4 to 10.2. Even in these samples, however, the stability and haze-free characteristics of the syrup are superior to the prior art syrups at comparable D.E.'s and solids concentrations.

An analysis of the high iodine ratios of Sample Nos. 10–13 is further evidence of the stability of the syrups against haze formation. Although Sample No. 10 is near the border line of the iodine ratio generally required to obtain a haze-free syrup, this sample still proved to be haze-free after 63 days.

The autoclaved samples appeared to have the same degree of stability against haze formation as the unautoclaved samples. It was noted, however, that upon autoclaving the dextrin, it turned darker in color but was thinner, and the previously insoluble portion of the dextrin was dissolved to a greater extent thatn the unautoclaved samples. The liquor was clearer and showed a partial break or phase separation. The autoclaved samples had a tendency to set back at room temperature, but were still thinner (flowed better) than the unautoclaved samples. After the enzyme was added, the unautoclaved liquors became thinner.

Most of the samples analyzed for optical transmittance at 600 nm. had a transmittance in excess of 90% at about 70% solids concentration. This result is especially surprising for a non-waxy corn starch hydrolysate at the D.E. and solids concentrations of the syrups tested.

Sample No. 7 was analyzed for carbohydrate composition and was found to be essentially the same as that of a product of comparable D.E. made from unmodified corn or white milo starch by the methods described in the prior art. The results are given in Table III as follows:

TABLE III

| Sample No. | D.E. | Quantitative Paper Chromatography | | | | | | |
|---|---|---|---|---|---|---|---|---|
| | | $DP_1$ | $DP_2$ | $DP_3$ | $DP_4$ | $DP_5$ | $DP_6$ | $DP_{7+}$ |
| 7 | 11.2 | 1.8 | 3.8 | 4.3 | 3.6 | 3.7 | 7.5 | 75.3 |
| A[a] | 10.0 | 0.3 | 3.4 | 4.3 | 3.5 | 3.6 | 7.0 | 77.9 |
| B[b] | 10.0 | 1.4 | 2.4 | 4.0 | 3.4 | 3.0 | 6.0 | 79.8 |
| C[c] | 10 | 1.0 | 5.0 | 6.5 | 5.5 | 4.5 | 9.0 | 69.0 |
| D[c] | 12 | 1.0 | 5.5 | 7.5 | 6.5 | 5.0 | 11.0 | 59.5 |

[a]Table III, Belgian Patent No. 708,104.
[b]Table VIII, Belgian Patent No. 708,104.
[c]Table , German Patent Publication No. 1,955,392.

As it can be seen from the data in Table III, the $DP_1$-$DP_6$ carbohydrate composition of the hdyrolysates of the present invention is substantially the same as the prior art at substantially the same D.E. However, the polydispersity value ($\overline{M}w/\overline{M}n$) of the prior art compositions as determined by gel permeation chromatography is generally greater than 25, whereas the polydispersity value of the hydrolysates of the present invention is less than about 20.

EXAMPLE 2

Starch hydrolysates were prepared by hydrolyzing commercially available canary potato and canary tapioca dextrins manufactured and sold by Stein-Hall and Company. The dextrins employed had the following characteristics:

TABLE IV

| Sample | Moisture % | pH | Solubles % d.b. | Color DMSO | D.E. | FAV Meq/ g.d.s. | Branching % |
|---|---|---|---|---|---|---|---|
| A | 9.2 | 3.9 | 99.9 | 440 | 1.5 | 1.12 | 14.8 |
| B | 4.3 | 4.0 | 99.7 | 322 | 2.1 | 1.33 | 16.9 |

A = 1212 Canary Potato Dextrin.
B = 14R Canary Tapioca Dextrin.

Each of the dextrins was slurried in water to a solids content of 27% d.s. in reactor pots. The pH of the slurries was adjusted to 7.0 and the reactor pots placed in a hot water bath to attemperate the slurries to a temperature of 83°C. To each reaction pot there was added 100 ppm, d.b., calcium to stabilize the enzyme. Each reaction pot was dosed with bacterial alpha-amylase enzyme preparation (HT-1000). Sample A was dosed with 0.03%, d.b., and Sample B was dosed with 0.06%, d.b. The enzymatic conversion was allowed to continue for 18 hours, whereupon the conversion was terminated by the addition of acid to reduce the pH below 4. The syrups were refined by filtering and treating with activated carbon. Sample A had a D.E. of 11.2 and Sample B had a D.E. of 12.4. The hydrolysates filtered rapidly and provided amber syrups that remained clear after more than a year's storage at a solids concentration of about 70%, dry basis.

EXAMPLE 3

This example illustrates an atttempt to prepare low D.E. starch hydrolysates by treating a corn dextrin with pancreatic amylase in place of bacterial alpha-amylase. White corn dextrin (Code 7381, manufactured and sold by CPC International Inc.) having a D.E. of 2.8 was dispersed in water in several reaction pots at a 16° Be concentration. The pH of each dispersion was adjusted to 7.0 and heated to a temperature of 65°C by placing the reaction pots in a hot water bath. 100 ppm, d.b., of calcium was added to each dispersion to stabilize the enzyme. To each of five reaction pots there was added 6, 8, 10, 12 and 15 ppm, d.b., pancreatin. The conversions were allowed to continue for 18 hours to achieve D.E.'s of 6.6, 7.6, 8.75, 9.9, and 11.3, respectively. The experiment was repeated using larger doses of pancreatin based upon the linear relationship of dosage to resulting D.E. Samples having a final D.E. of 10.0, 12.7, 14.1 and 16.6 were obtained. The hydrolysates were refined and concentrated to a solids content of 70% to evaluate their stability against haze formation. The results of the haze formation analysis are as follows:

| Syrup D.E. | Clarity Stability |
|---|---|
| 10.0 | Turned opaque in 8 days. |
| 12.7 | Formed heavy haze in 11 days. |
| 14.1 | Slight haze formed in 18 days, eventually turned opaque and solid. |
| 16.6 | Slight haze formed in 25 days, very hazy but still fluid after 116 days. |

The results in the above data indicate that a stable syrup cannot be prepared by hydrolyzing dextrins with pancreatin even at a D.E. level as high as 16.6. For comparison, 10–12 D.E. syrups of excellent clarity were obtained from the same dextrin using bacterial alpha-amylase. See Example 1. This difference is attributed to the marked difference in the action patterns of the two types of alpha-amylases.

EXAMPLE 4

Several experiments were conducted to demonstrate that a stable syrup cannot be obtained by hydrolyzing dextrins with acid rather than bacterial alpha-amylase. The experiments were conducted as follows.

Slurries of dextrins were prepared by dispersing a corn starch dextrin (characterized as having a pH of 4.8, a moisture content of 2.4%, 95.3% d.b. solubles, a pH of 2.6, a FAV in meq/g.d.s. of 151 and 14.2% branching) in water to a concentration of 16° Be. The slurries were adjusted to a pH of 2.2 with hydrochloric acid and heated under reflux. Hydrolysates from the samples were processed to syrups of 70% solids. The results are as follows:

TABLE V

| Sample No. | Catalyst | Reaction Time Hours | Finished D.E. | Syrup Stability Days |
|---|---|---|---|---|
| 1 | HCl | 2.0 | 10.2 | <2 |
| 2 | HCl | 3.5 | 14.7 | <5 |
| Control | HT-1000 | — | 9.6 | >90 |

The above results indicate that 10–15 D.E. syrups prepared by acid hydrolysis haze rapidly whereas the 10 D.E. syrup prepared by enzyme hydrolysis is resistant to haze formation. This difference is attributed mainly to the mode of action of the two catalysts. Bacterial alpha-amylase does not hydrolyze the alpha, 1–6 linkage and hence the reaction products are highly branched. In contrast, acid hydrolyzes both the alpha, 1–4 and the alpha, 1–6 linkages with the alpha, 1 6 being about 25% as susceptible to hydrolysis as the alpha, 1–4. (See *Starch: Chemistry and Technology*, Vol. I, p. 190, Whistler, R. L. and Paschall, E. F.) In addition, steric hindrance probably plays a role in enzymatic hydrolysis. For example, alpha, 1–6 linkages in close proximity to each other may act as a barrier to enzymatic hydrolysis and thus prevent scission of the alpha, 1–4 bonds between the branched points. Supporting evidence for this view is the finding that a pentassaccharide is the smallest alpha-limit dextrin that is formed when starch is hydrolyzed with bacterial alpha-amylase. See, for example, W. J. Whelan, Die Starke, 12, 358-364 (1960).

EXAMPLE 5

Preparation of Starch Hydrolysates From Dextrins Produced In A 10-Inch Diameter Agitated Fluid Bed a. Preparation of Starch Dextrins Several dextrin samples were prepared in a 10-inch diameter agitated fluidized bed by the procedure that follows.

Corn starch was placed in a ribbon blender and sprayed with aqueous hydrochloric acid (0.36% aqueous hydrochloric acid on a dry starch basis) while the starch was blended continuously. The spray nozzles were positioned so that the spray patterns of the two nozzles covered the entire length of the blender with a mininum overlap at the center. The acid was gravity fed to the nozzles and atomized by 18 psig air. The blender, equipped with a variable speed agitator ranging from 80–200 rpm, was run at the lowest agitator speed, 80 rpm, to reduce dusting problems. Acid addition times varied according to the desired acid concentrations, but all batches were blended for at least 30 minutes after completion of the acid addition.

The blended and treated starch was then separated into portions to be charged into the agitated fluid bed, which had been preheated to about 135.5°C (250°F) while the starch was being treated with acid. The sparging gas was preheated to a minimum temperature of 136.6°C (260°F) by routing it through a super heater.

When the minimum bed temperature and sparging gas temperature were obtained, the acid-treated starch was charged into the fluid bed through the top. The bed was continuously agitated during charging. The sparging gas was diverted to the atmosphere until the bed was fully charged, when dry air or humid air was used. When steam was used as the sparging gas, it was routed into the fluidizing chamber during the charging period. Steam, air, and a mixture of steam and air were all used at various times as the sparging gas. Relative humidity of the steam-air mixtures was determined from wet and dry bulb temperatures taken at the sparging gas by-pass valve after the sparging gas had been heated. The sparging gas entered the fluidizing chamber through a centered brass plate at the bottom of the chamber. Vapors were pulled from the chamber by vacuum. A centered brass band located at the top of the chamber was used as a dust collector. Dust which collected on the brass band was removed by scrapers attached to the agitator shaft and fell back into the chamber. An agitator with a plurality of horizontal blades was used to prevent channelling and dead spots.

Time zero was recorded as the time when the bed was fully charged with the sparging gas flowing into the chamber. Samples were taken at various times by partially removing a plug from the bottom of the fluidized chamber and allowing the necessary quantity of reacted starch to flow to an open and flat collection means. The plug was reseated and the sample was spread on the collection means to promote cooling at a rapid rate. Samples taken from the bed between 104.4°C (220°F) and 115.5°C (240°F) cooled below 93.3°C (200°F) within two and one-half minutes. Samples taken directly in a closed container required from 13–21 minutes to cool below 93.3°C when taken from the bed at the same temperature range. The cooling of the reacted starch terminated the reaction.

The processing conditions employed in preparing the various batches of dextrin in the 10-inch diameter agitated fluidized bed reactor are given in Table VI. In the table, the reaction variables are temperature, type of fluidizing gas, starch moisture, acid concentration and reaction time.

TABLE VI

DEXTRINIZATION PROCESSING CONDITIONS EMPLOYING 10-INCH AGITATED FLUID BED

| Run Number | Starch Moisture, % | Air Type | HCl, % d.b. | Time, Minutes | Temp., °C |
|---|---|---|---|---|---|
| 1 | 12.0 | Dry | 0.36 | 20 | 98.9 |
| 2 | 12.0 | Dry | 0.36 | 35 | 108.9 |
| 3 | 12.0 | Dry | 0.36 | 50 | 114.3 |
| 4 | 12.0 | Dry | 0.36 | 65 | 116.2 |
| 5 | 11.3 | Humid | 0.36 | 54 | 116.7 |
| 6 | 11.3 | Humid | 0.36 | 84 | 122.8 |
| 7 | 11.3 | Humid | 0.36 | 114 | 123.3 |
| 8 | 11.3 | Humid | 0.36 | 124 | 123.3 |
| 9 | 10.4 | Humid | 0.09 | 120 | 118.3 |
| 10 | 10.7 | Dry | 0.09 | 21 | 111.7 |
| 11 | 10.7 | Dry | 0.09 | 24 | 113.3 |
| 12 | 10.7 | Dry | 0.09 | 27 | 115.0 |
| 13 | 10.7 | Dry | 0.09 | 42 | 119.4 |
| 14 | 10.7 | Dry | 0.09 | 57 | 120.5 |
| 15 | 10.7 | Dry | 0.09 | 72 | 121.1 |
| 16 | 7.8 | Dry | 0.09 | 46 | 115.0 |
| 17 | 7.8 | Dry | 0.09 | 60 | 117.2 |
| 18 | 7.8 | Dry | 0.09 | 73 | 118.3 |
| 19 | 7.8 | Dry | 0.09 | 80 | 119.4 |
| 20 | 11.7 | Humid | 0.09 | 30 | 108.9 |
| 21 | 11.7 | Humid | 0.09 | 50 | 117.8 |
| 22 | 11.7 | Humid | 0.09 | 70 | 120.0 |
| 23 | 11.7 | Humid | 0.09 | 90 | 121.1 |

Each of the starch dextrins was analyzed to determine the changes occurring during the course of the dextrinization. These changes follow patterns well-established for dextrins prepared by conventional commercial processes. (See, for example, R. B. Evans and O. B. Wurtburg, *Starch: Chemistry and Technology*, Vol. 2, Chapter XI, 1967, pp. 266–270.) The two major changes that occur during dextrinization are:

1. a decrease in molecular size as reflected by an increase in solubility and a decrease in viscosity, and
2. an increase in the degree of branching which can be calculated from the formic acid liberated upon periodate oxidation.

The analysis for each sample of the starch dextrins prepared by the method described hereinabove is set forth in Table VII.

TABLE VII

PRODUCT ANALYSIS OF DEXTRINS PRODUCED FROM 10-INCH AGITATED FLUID BED

| Run Number | D.E. | Moisture, % | Solubles, % d.b. | pH | FAV, meq/g d.s. | Branching, % | IAV | DMSO Color, Calc. 40°Be | Viscosity, cp R.T. | Viscosity, cp 83°C |
|---|---|---|---|---|---|---|---|---|---|---|
| 1 | 7.3 | 3.7 | 92.7 | 2.6 | 1.37 | 5.2 | 0.51 | 18 | 425 | 60 |
| 2 | 6.8 | 1.2 | 94.2 | 2.7 | 1.63 | 11.8 | 0.37 | 29 | 400 | 30 |
| 3 | 5.0 | 2.2 | 96.0 | 2.8 | 1.52 | 13.3 | 0.33 | 170 | 100 | 25 |
| 4 | 4.1 | 0.4 | 99.4 | 3.0 | 1.39 | 13.3 | 0.30 | 489 | n.d. | n.d. |
| 5 | 6.5 | 1.5 | 95.7 | 2.5 | 1.65 | 12.0 | 0.35 | 99 | 225 | n.d. |
| 6 | 4.5 | 1.1 | 97.2 | 2.6 | 1.50 | 14.2 | 0.32 | 487 | n.d. | n.d. |
| 7 | 4.8 | 0.5 | 97.6 | 2.7 | 1.47 | 13.0 | 0.31 | 750 | n.d. | n.d. |
| 8 | 4.2 | 0.6 | 99.0 | 2.8 | 4.8 | 14.6 | 0.31 | 965 | n.d. | n.d. |
| 9 | 3.6 | 1.2 | n.d. | 3.3 | 1.05 | 8.8 | 0.48 | 22 | 65 | 32 |
| 10 | 3.3 | 4.2 | 87.8 | 3.2 | 0.71 | 3.8 | 0.93 | 17 | 15 | 65 |
| 11 | 4.2 | 3.2 | 90.9 | 3.2 | 0.90 | 4.8 | 0.76 | 18 | 23 | 49 |
| 12 | 4.7 | 3.0 | 92.2 | 3.2 | 0.96 | 4.6 | 0.65 | 17 | 43 | 31 |
| 13 | 4.6 | 1.9 | 97.8 | 3.3 | 1.21 | 9.3 | 0.43 | 19 | 500 | 21 |
| 14 | 4.2 | 1.3 | 98.9 | 3.4 | 1.13 | 8.7 | 0.40 | 31 | 200 | 18 |
| 15 | 4.0 | 0.8 | 98.7 | 3.5 | 1.19 | 10.2 | 0.38 | 34 | 115 | 25 |
| 16 | 4.2 | 1.7 | 91.9 | 2.8 | 1.13 | 8.7 | 0.48 | 30 | 800 | 27 |
| 17 | 4.0 | 0.5 | 94.6 | 2.8 | 1.17 | 9.8 | 0.39 | 30 | 275 | 18 |
| 18 | 3.4 | 1.0 | 94.5 | 2.9 | 1.19 | 11.6 | 0.38 | 26 | 190 | 15 |
| 19 | 3.3 | 0.3 | 94.0 | 3.0 | 1.15 | 11.1 | 0.36 | 49 | 130 | 14 |
| 20 | 1.9 | 4.5 | 44.8 | 3.6 | 0.59 | 5.2 | 1.16 | 17 | 10 | 180 |
| 21 | 3.4 | 2.3 | 90.1 | 3.6 | 0.90 | 6.7 | 0.71 | 18 | 30 | 33 |
| 22 | 3.5 | 1.7 | 93.7 | 3.7 | 1.00 | 8.2 | 0.56 | 14 | 125 | 23 |
| 23 | 3.4 | 2.1 | n.d. | 3.7 | 0.95 | 7.6 | 0.54 | 21 | 130 | 22 |

Certain special methods of analysis were employed which are reflected in Table VII and in other analyses of dextrins and/or starch hydrolysates described herein.

The following is a brief description of these analytical techniques.

Solubles

Accurately weigh to 0.1 mg., 5 grams of dextrin and 2 grams of Celite into a 150-ml. beaker. Add 100 ml. of 60°C water and disperse by agitating for 5 minutes with a magnetic stirrer. Then, filter the sample with suction and wash 100 ml. of water which has been heated to a temperature of 60°C (140° F). The amount of solubles present is calculated as follows:

$$\text{Solubles, \% } d.b. = \frac{\text{wt. dextrin, } d.b. - \text{wt. insolubles, } d.b.}{\text{wt. dextrin, } d.b.} \times 100$$

The weight of the insolubles only refers to the insoluble dextrins, and does not include Celite and filter paper.

Color, DMSO

Prepare a 90% dimethyl sulfoxide (DMSO) on a V/V basis by adding the proper amount of water to a volumetric flask and then dilute to the mark with dimethyl sulfoxide (DMSO). Since heat is generated on fixing, cool the sample to room temperature before final dilution to the mark. Dissolve 10 grams, d.b., of dextrin in about 80 ml. of rapidly stirred 90% DMSO. If necessary, heat to 65.5°C (150°F) to effect complete dissolution. Cool the sample to room temperature, quantitatively transfer to a 100-ml. volumetric flask and dilute to the mark with 90% DMSO. Filter by gravity through a Whatman 2V paper and determine color using 90% DMSO as a blank in place of distilled water. Calculate color on a 40° Be basis by multiplying by the factor 105/10.

Use of 90% DMSO as a solvent was necessary because many of the dextrin samples are not completely soluble in water. Preliminary tests indicate that low D.E. products, completely soluble in water, exhibit colors that are 30–40% higher in 90% DMSO than in water. It is presumed that the same relationship is true for dextrins.

Iodine Absorbancy Value (IAV)

Prepare an aqueous iodine stock solution containing 0.200 gram of resublimed iodine and 2.000 grams of reagent grade potassium iodide per 100 ml. Then, prepare an aqueous stock solution of the sample at the concentration shown in the table immediately following. The recommended concentration is dependent on sample D.E. and product type. The sample should be weighed to the nearest mg. Pipette a 10-ml. aliquot of the stock solution into a 500-ml. volumetric flask, add about 450 ml. of distilled water and mix. Again, by pipette, add 5 ml. of the iodine reagent and dilute to mark with distilled water. Prepare an iodine reagent blank in an identical manner. Place the sample and blank in a 25.0° ± 0.05°C constant temperature water bath for about 30 minutes. Remove and immediately determine absorbancy of the sample against the blank at 500 mm. in a Beckman Spectrophotometer. Use a 4-cm. cell and multiply by 1.25 to correct to a 5-cm. cell basis. If the complete spectro curve is desired, use a recording Beckman Dk-2 Spectrophotometer and a 5-cm. cell depth. Determine absorbancy over the wavelength range of 350–700 mm.

The iodine absorbancy value (IAV) is arbitrarily defined as the absorbancy at 500 mm. expressed on a 5-cm. cell basis and calculated to a concentration of 1 mg. of dry substance per ml.

The following modification of the above procedure is generally desirable for determining the iodine absorbancy value (IAV) for dextrins.

On a dry basis, weight 200 mg. of dextrin into a 50-ml. beaker and dissolve in 10.0 ml of 0.50 N sodium hydroxide. Using distilled water, quantitatively transfer the sample into a 100-ml. volumetric flask and dilute to mark. Pipette a 10-ml. aliquot into a 500ml. volumetric flask, add about 400 ml. of distilled water and acidify by adding via pipette 3.0 ml. of 0.20 N hydrochloric acid. Add the prescribed iodine reagent and follow the method as described above. The second modification is to determine the absorbancy at 550 mm. instead of 500. The final dextrin concentration is 0.04 mg./ml.

The following table illustrates the relationship between D.E. and the stock solution, referred to hereinabove.

TABLE VIII

| Sample D.E. | Stock Solution g.d.s. | Volume, ml. | Sample Concentration mg. d.s./ml. |
|---|---|---|---|
| Regular Starch-Based Products | | | |
| 5 | 2 | 1,000 | 0.04 |
| 10 | 2 | 200 | 0.20 |
| 15 | 6 | 100 | 1.20 |
| 19 | 12 | 100 | 2.40 |
| Waxy Starch-Based Products | | | |
| 5 | 2 | 500 | 0.08 |
| 10 | 2 | 100 | 0.40 |
| 15 | 8 | 100 | 1.60 |
| 19 | 12 | 100 | 2.40 |
| Corn Dextrin-Based Syrups | | | |
| 10–16 | 5 | 100 | 1.00 | b. Enzymatic Hydrolysis of Starch Dextrins

The starch dextrins prepared by the method described hereinabove were enzymatically hydrolyzed using the following procedure.

As a preliminary experiment, a starch dispersion was prepared by adding the starch dextrin of Example 5(a), Dextrin Run No. 7 (D.E. 4.8) to water at a concentration of 16° Be. The starch dextrin slurry was neutralized to a pH of about 7.0. Several aliquot samples of the starch dextrin slurry were placed in enzymatic reaction vessels and heated to a temperature of 83°C in a hot water bath. Each of the reaction vessels containing the starch dextrin slurry was dosed with varying amounts of a bacterial alpha-amylase enzyme preparation (HT-1000) while stirring. In some of the samples, an aqueous solution (0.1 M) of calcium chloride was added in varying amounts. The following data is illustrative of the increased effectiveness calcium has on the enzymatic conversion of the starch dextrin with bacterial alpha-amylase.

TABLE IX

| Sample No. | Calcium Added ppm, d.b. | HT-1000 % d.b. | Hydrolysate D.E. | Increase in D.E. |
|---|---|---|---|---|
| 1 | 0 | 0.006 | 5.7 | 0.9 |
| 2 | 50 | 0.006 | 8.5 | 3.7 |
| 3 | 100 | 0.006 | 10.9 | 6.1 |
| 4 | 100 | 0.004 | 9.6 | 4.8 |

TABLE IX-continued

| Sample No. | Calcium Added ppm, d.b. | HT-1000 % d.b. | Hydrolysate D.E. | Increase in D.E. |
|---|---|---|---|---|
| 5 | 100 | 0.008 | 11.7 | 6.9 |

Based upon the foregoing data, the enzymatic conversions were conducted as follows.

Each of the starch dextrins was dispersed in 1-liter stainless steel beakers in 450 ml. of water (187 grams of dextrin "as is") to provide a 600 ml.-16° Be dispersion. The pH of the dispersion was adjusted to 7.0 with 2 N sodium hydroxide and on a dextrin d.b., there was added 100 ppm of calcium as an aqueous solution of the chloride salt (4.68 ml. of 0.1 M calcium chloride). The pH was again checked and readjusted to 7.0 when necessary. The viscosity of the dextrin dispersion at room temperature was measured using a Brookfield viscometer. Each of the samples was placed in a water bath heated to a temperature of 80°C and stirred for 15 minutes. The samples were removed from the hot water bath and the viscosity of the sample was determined using spindle no. 1. The samples were then returned to the 83°C water bath and the pH was again checked and adjusted to a pH of 7.0 if necessary. Thereafter, the required amount of bacterial alpha-amylase (Takamine HT-1000 bacterial alpha-amylase, a bacterial alpha-amylase preparation manufactured and sold by Miles Chemical Laboratory) was added. Activity of the HT-1000 used was 3800 U/G. The required enzyme dosage varied for different dextrins and was dependent upon the desired product D.E. After one hour of enzymatic hydrolysis, the pH was again checked and readjusted to a pH of 7.0 if necessary. After the desired reaction period was complete, the enzyme was inactivated by lowering the pH to 3.9–4.0 and the samples were held at 83°C for 10 minutes. The samples were then transferred to a 60°C water bath, equilibrated and filtered under vacuum. The filtration rates are expressed in one of two ways:

1. time require to obtain pad dryness or
2. if filtration is incomplete at the end of 60 minutes, measure and record volume of filtrate obtained in 60 minutes.

Aliquots of the filtrates were analyzed for D.E. The major portion of the filtrate was treated with activated carbon for 30 minutes at 60°C and at a pH of 4.3, followed by filtering under vacuum using a water aspirator at a 58°C water bath, the final filtrates were evaporated under reduced pressure to a solids content of about 70%. The final syrups were transferred to 4-oz. bottles and capped and stored at room temperature for clarity stability observations.

The iodine absorbancy value (IAV) was also determined on many of the final syrup products.

The results of the above-described enzymatic hydrolysis of the starch dextrins and the relative amounts of the bacterial alpha-amylase preparation added to each starch dextrin sample are set forth in Table X.

TABLE X

LOW D.E. SYRUPS FROM DEXTRINS PRODUCED FROM 10-INCH AGITATED FLUID BED

| Dextrin Run Number | HT-1000, % d.b. | D.E. Dextrin | D.E. Syrup | Color, Visual | Filtration Rate | | Clarity Stability, days | IAV |
|---|---|---|---|---|---|---|---|---|
| 1 | 0.0035 | 7.3 | 13.0 | Light Yellow | 300 | ml. | 1 | n.d. |
| 2 | 0.004 | 6.8 | 11.8 | Dark Yellow | 310 | sec. | 21 | 0.41 |
| 3 | 0.010 | 5.0 | 12.6 | Dark Amber | 43 | sec. | >90 | 0.06 |
| 4 | 0.015 | 4.1 | 11.5 | Black | 34 | sec. | >90 | n.d. |
| 5 | 0.005 | 6.5 | 11.6 | Amber | 38 | sec. | >90 | 0.26 |
| 6 | 0.010 | 4.5 | 11.6 | Black | 28 | sec. | >90 | n.d. |
| 7 | 0.010 | 4.8 | 10.2 | Black | 32 | sec. | >90 | n.d. |
| 8 | 0.010 | 4.2 | 9.8 | Black | 30 | sec. | >90 | n.d. |
| 9 | 0.0050 | 3.6 | 11.2 | Light Yellow | 220 | ml. | 7 | 0.44 |
| 9A | 0.0065 | 3.6 | 12.3 | Light Yellow | 250 | ml. | 63 | 0.31 |
| 10 | 0.0040 | 3.3 | 10.7 | Light Yellow | n.d. | | 1 | n.d. |
| 11 | 0.0035 | 4.2 | 10.2 | Light Yellow | 250 | ml. | 1 | 2.02 |
| 12 | 0.0040 | 4.7 | 11.0 | Light Yellow | 370 | ml. | 1 | n.d. |
| 13 | 0.0050 | 4.6 | 10.8 | Light Yellow | 400 | ml. | 1 | 0.48 |
| 14 | 0.0065 | 4.2 | 11.0 | Light Yellow | 54 | min. | >90 | 0.24 |
| 15 | 0.0035 | 4.0 | 8.5 | Light Yellow | n.d. | | 1 | 0.59 |
| 15A | 0.0050 | 4.0 | 9.6 | Light Yellow | — | | 36 | 0.38 |
| 16 | 0.005 | 4.2 | 11.0 | Light Yellow | 320 | ml. | 10 | 0.53 |
| 17 | 0.0065 | 4.0 | 11.7 | Yellow | 400 | ml. | 22 | 0.17 |
| 18 | 0.008 | 3.4 | 12.2 | Yellow | 400 | ml. | >90 | 0.09 |
| 19 | 0.009 | 3.3 | 12.0 | Yellow | 420 | ml. | >90 | 0.06 |
| 20 | 0.005 | 1.9 | 11.6 | Very Light Yellow | 190 | ml. | 1 | 1.51 |
| 21 | 0.006 | 3.4 | 12.2 | Light Yellow | 325 | ml. | 2 | 0.63 |
| 22 | 0.007 | 3.5 | 12.2 | Light Yellow | 350 | ml. | 27 | 0.34 |
| 23 | 0.008 | 3.4 | 13.0 | Light Yellow | 355 | ml. | 48 | 0.26 | c. Enzymatic Conversion of Starch Dextrins

The procedure outlined above in Example 5(b) was repeated using different amounts of the bacterial alpha-amylase preparation. As the starch dextrins used as substrates, Dextrin Run Numbers 10, 20 and 21 were employed. Table XI provides the amount of enzyme dosage used and the various analytical results obtained from the dextrin and starch hydrolysate samples.

TABLE XI

LOW D.E. SYRUPS FROM DEXTRINS PRODUCED FROM 10-INCH AGITATED FLUID BED

| Dextrin Run Number | HT-1000, % d.b. | D.E. Dextrin | D.E. Syrup | Color, 40°Be | Filtration Rate | Clarity Stability, Days | Dextrin Branching, % | IAV Dextrin | IAV Syrup |
|---|---|---|---|---|---|---|---|---|---|
| 10 | 0.008 | 3.3 | 15.3 | 7.8 | 270 ml. | 2 | 3.8 | 0.93 | 0.50 |
| 20 | 0.008 | 1.9 | 14.5 | 6.8 | 220 ml. | 2 | 5.2 | 1.16 | 0.53 |

TABLE XI-continued

LOW D.E. SYRUPS FROM DEXTRINS PRODUCED FROM 10-INCH AGITATED FLUID BED

| Dextrin Run Number | HT-1000, % d.b. | D.E. Dextrin | D.E. Syrup | Color, 40°Be | Filtration Rate | Clarity Stability, Days | Dextrin Branching, % | IAV Dextrin | IAV Syrup |
|---|---|---|---|---|---|---|---|---|---|
| 21 | 0.010 | 3.4 | 16.0 | 6.9 | 300 ml. | 54 | 6.7 | 0.71 | 0.22 |

EXAMPLE 6

Preparation Of Starch Hydrolysates From Dextrins Produced From 7-Tube Fluid Bed — Batchwise a. Preparation of Starch Dextrins Several starch dextrins were prepared batchwise in a 7-tube fluid bed by the procedure that follows.

Corn starch was acidified by two different methods. Initially, the starch was acidified with 36% d.b. hydrochloric acid sprayed onto the starch while the starch was agitated in a ribbon blender, as more fully described in Example 5. The second method employed consisted of employing anhydrous hydrogen chloride as the acidifying agent. A double conical blender was used to agitate the starch by this latter method. This latter method proved to be the preferred technique and was employed to acidify the starch. Employing this latter technique to prepare the starch dextrins, the double conical blender was charged with corn starch having a moisture content ranging from 10% to 12%. The desired acid concentration was determined assuming the blender charge had a moisture content of 11%. The blender was agitated for an additional 30 minutes after the acid addition was completed. The acidified starch was then removed from the blender and sifted through a 20-mesh screen on a vibrating screener. The oversize portion of the acidified starch was discarded and the portion that went through the 20-mesh screen was placed in containers to be dextrinized.

A 7-tube fluid bed was preheated at 148.8°C (300°F) for 1 hour with heated fluidizing air flowing through the tubes. Starch was fed into the upper half of the fluid bed through a VIBRASCREW Feeder. The fluidizing air was fed into the lower half of the fluid bed through a plurality of orifices. The bed was heated by pressurized steam heated jacket surrounding the tubes. The 7-tube bed was set at the highest feed rate. The reacted product was conveyed through the overflow discharge to a rotary air lock on a pneumatic cooling tube. Air and product were separated in a product cyclone. The product was discharged through a rotary air lock into a 100-pound trays to be used to prepare the low D.E. starch hydrolysates. The air was discharged to the atmosphere through a wet scrubber to remove the last traces of dust.

Table XII provides the operating conditions used in the preparation of the starch dextrins. The starch dextrins prepared in the 7-tube fluid bed were characterized in the same manner as those produced in the 10-inch diameter agitated bed described in Example 5. The data is provided in Table XIII.

Periodate oxidation analyses and D.E. were used to calculate the degree of branching for each of the "dextrins". It was observed that the dextrin products prepared in the 10-inch diameter agitated bed having a degree of branching of from 8.5% to 11.2% had a DSMO color range of 26 to 170. The products from batch reactions in the 7-tube fluid bed having a degree of branching of 10.1% to 13.1% had a DMSO color range of 21 to 42.

TABLE XII

DEXTRINIZATION PROCESSING CONDITIONS EMPLOYING 7-TUBE FLUID BED - BATCHWISE

| Run Number | Starch Moisture, % | Air Type | HCl, % d.b. | Time in Minutes | Temp. °C |
|---|---|---|---|---|---|
| 1 | 11.8 | Dry | 0.07 | 10 | 175.6 |
| 2 | 11.8 | Dry | 0.07 | 15 | 177.8 |
| 3 | 11.8 | Dry | 0.07 | 20 | 167.2 |
| 4 | 11.1 | Dry | 0.07 | 10 | 157.2 |
| 5 | 11.2 | Dry | 0.07 | 15 | 167.2 |
| 6 | 11.3 | Dry | 0.07 | 20 | 147.2 |

TABLE XIII

PRODUCT ANALYSIS OF DEXTRINS PRODUCED FROM 7-TUBE FLUID BED - BATCHWISE

| Run Number | D.E. | Moisture, % | Solubles, % d.b. | pH | FAV meq/g d.s. | Branching, % | IAV | DMSO Color, Calc. 40°Be | Viscosity, cp R.T. | Viscosity, cp 83°C |
|---|---|---|---|---|---|---|---|---|---|---|
| 1 | 2.0 | 3.2 | 94.5 | 3.1 | 1.01 | 11.8 | 0.43 | 21 | 43 | 14 |
| 2 | 1.8 | 1.1 | 96.0 | 3.1 | 1.12 | 14.1 | 0.35 | 41 | 40 | 9 |
| 3 | 2.2 | 1.7 | 96.1 | 3.0 | 1.16 | 13.8 | 0.36 | 37 | 47 | 11 |
| 4 | 2.6 | 1.5 | 93.8 | 2.9 | 1.07 | 11.4 | 0.47 | 28 | 38 | 18 |
| 5 | 2.9 | 4.1 | 95.7 | 2.9 | 1.14 | 11.9 | 0.52 | 42 | 38 | 25 |
| 6 | 2.4 | 3.2 | 91.2 | 2.9 | 1.06 | 11.7 | 0.43 | 28 | 45 | 18 | b. Enzymatic Hydrolysis of Starch Dextrins

The starch dextrins prepared in the 7-tube fluid bed — batchwise — were enzymatically hydrolyzed using the same procedure described in Example 5(b).

The characteristics of the low D.E. starch hydrolysates and the relative amounts of the bacterial alpha-amylase preparation added to each starch dextrin are set forth in Table XIV.

TABLE XIV

LOW D.E. SYRUPS FROM DEXTRINS PRODUCED FROM 7-TUBE FLUID BED - BATCHWISE

| Dextrin Run Number | HT-1000, % d.b. | D.E. Dextrin | D.E. Syrup | Color, Visual | Filtration Rate | Clarity Stability, days | IAV |
|---|---|---|---|---|---|---|---|
| 1A | 0.007 | 2.0 | 9.9 | Yellow | 365 ml. | >90 | 0.20 |

TABLE XIV-continued
LOW D.E. SYRUPS FROM DEXTRINS PRODUCED FROM 7-TUBE FLUID BED - BATCHWISE

| Dextrin Run Number | HT-1000, % d.b. | D.E. Dextrin | D.E. Syrup | Color, Visual | Filtration Rate | Clarity Stability, days | IAV |
|---|---|---|---|---|---|---|---|
| 1B | 0.007 | 2.0 | 10.0 | Light Yellow | n.d. | >90 | 0.16 |
| 2 | 0.008 | 1.8 | 9.2 | Yellow | 350 ml. | >90 | 0.12 |
| 3A | 0.009 | 2.2 | 10.9 | Dark Yellow | 345 ml. | >90 | 0.09 |
| 3B | 0.009 | 2.2 | 10.3 | Light Yellow | n.d. | >90 | 0.08 |
| 4 | 0.006 | 2.6 | 9.2 | Yellow | 285 ml. | >90 | 0.27 |
| 5 | 0.007 | 2.9 | 10.9 | Yellow | 250 ml. | >90 | 0.15 |
| 6 | 0.008 | 2.4 | 11.2 | Yellow | 290 ml. | >90 | 0.10 |

In order to ascertain the optimum refining procedure for the dextrin hydrolysates, two 6-liter batches of about 10 D.E. hydrolysates were prepared; one from Dextrin Run Number 1A and one from Dextrin Run Number 3A (Table XIV). The latter dextrin hydrolysate was higher in color and more extensively branched. In each case, the refining sequence was: carbon treatment-ion exchange-carbon treatment. The ion exchange resins employed and conditions of operation were as follows:

1. Single-Pass System — 1st. column 300 ml. of Duolite C-3, 2nd. column 200 ml. of Amberlite IRA-93.
2. Operation Conditions — ambient temperature, flow rate 2 B.V./hr., liquor pH 4.3, ca. 16° Be.

Two different methods of ion exchange operation were employed in refining the syrups. The hydrolysate from Dextrin Run Number 1A (19 B.V.) was percolated through the system twice, the resins being regenerated between percolations. On the initial pass, the pH dropped to 4.5 after passage of 11.8 B.V. and then continued to drop, leveling off at 3.1 A negative silver nitrate test for chloride ion and a leveling off pH of 3.1 each indicates the breakthrough of organic acids at 11.8 B.V. On the second pass, organic acids broke through at 6–7 B.V. and the pH then decreased gradually to 3.3. All throughputs are expressed on a 16° Be basis.

In contrast, the hydrolysate from Dextrin Run Number 3A was passed through the ion exchange system until effluent pH dropped to 4.5. At this point the columns were sweetened-off and the sweetwater added to the supply liquor. The ion exchange columns were regenerated and the process repeated twice. Breakthrough volumes in the three successive runs were 4.6, 4.5 and 4.8 (16° Be basis). A composite was made of the three effluents prior to carbon treatment. The stepwise removal of color from each dextrin hydrolysate is shown below:

TABLE XV

| Stage | Color, 40° Be | Color Removed, % Stepwise | Color Removed, % Cumulative |
|---|---|---|---|
| 10.0 D.E. Hydrolysate - Dextrin Run Number 1A | | | |
| Original | 112.4 | — | — |
| 1.0% Darco S-51 | 51.1 | 54.5 | 54.5 |
| Ion exchange, 1st. Pass | 12.7 | 75.1 | 88.7 |
| Ion exchange, 2nd. Pass | 5.1 | 59.8 | 95.5 |
| 1.0% Darco S-51 | 4.3 | 15.7 | 96.2 |
| 10.3 D.E. Hydrolysate - Dextrin Run Number 3A | | | |
| Original | 146.9 | — | — |
| 1.0% Darco S-51 | 82.9 | 43.6 | 43.6 |
| Ion exchange | 7.3 | 91.2 | 95.0 |
| 3.0% Darco S-51 | 4.1 | 43.8 | 97.2 |

Decolorizing data indicate that each refining sequence gives finished syrups having colors of 4.1–4.3. Syrups of significantly lower color can probably be obtained by minimizing the destruction reaction during dextrinization and by improving refining techniques. Ash content of each ion exchanged syrup was 0.03%, d.b., or less indicating efficient demineralization. In double-pass operation, throughput of 16° Be liquor was about 19 bed volumes based on anion-exchange resin volume of 200 ml. On a 30° Be basis, this is equivalent to a throughput of 8.0 bed volumes.

Efficiency of the ion exchange system for removing acids is shown below:

TABLE XVI

| | Hydrolysate Acidity, meq/100 g.d.s. | | | | | |
|---|---|---|---|---|---|---|
| | Dextrin Run No. 1A | | | Dextrin Run No. 3A | | |
| Acidity | Initial | Final | Removal, % | Initial | Final | Removal, % |
| HCl | 3.5 | 0.13 | 96.3 | 3.6 | 0.33 | 90.8 |
| Organic | 2.8 | 0.45 | 83.9 | 2.7 | 0.33 | 87.8 |
| Total | 6.3 | 0.58 | 90.8 | 6.3 | 0.66 | 89.5 |

These results indicate that about 44% of the acidity in the initial dextrin hydrolysates is attributed to organic acids. In an attempt to identify the kind of organic acids present, the anion exchange resin (2nd. pass, Dextrin Run Number 1A) was eluted with 1 N sodium hydroxide and the eluate decationized and dried. The dried material was derivatized and the soluble portion was found to contain three major components and at least eight minor ones. One major peak was identified as representing oxalic acid and one minor peak as tartaric acid. Analysis by I.R. also showed a strong carboxylic acid group response.

The logical conclusion is that these organic acids are formed during dextrinization. To gain insight into their nature, a sample of Dextrin Run Number 1A was potentiometrically titrated with standardized alkali and then back-titrated with standardized acid. The titration curves show marked hysteresis suggesting the formation of organic acids by opening of lactone type structures present in the dextrin. The shape of the titration curves and the fact that each curve exhibits an inflection point at pH 8.3 are characteristic for organic acids. Thus, about 22% of the acids in the dextrin (0.66 out of 2.94 meq/100 g.d.s.) are probably present in a lactone form.

EXAMPLE 7

Preparation Of Starch Hydrolysates From Dextrins In A 7-Tube Fluid Bed — Continuous a. Preparation of the Starch Dextrin Several starch dextrins were prepared in a 7-tube fluid bed in a continuous manner by the procedure that follows.

Corn starch was acidified by anhydrous hydrogen chloride in the manner set forth in Example 6(a). The acidified starch was charged into the upper half of a 7-tube fluid bed which had been preheated to a temperature of 148.8°C (300°F), by the fluidizing air flowing through the tubes. The feed rate was limited by the reaction temperature in the bed when the 7-tube fluid bed was used as a continuous reactor. Therefore, in order to obtain the desired reaction temperature and residence time, the feeder was set at the highest rate at which the reaction temperature could be maintained and any reductions in residence time was made by decreasing the bed volume. This was accomplished by increasing the flow rate of the fluidizing air to the bed. The reacted product was recovered in the manner set forth in Example 6(a).

Table XVII indicates the operating conditions, employed to effect the dextrinization and characteristics of the starting material.

TABLE XVII

DEXTRINIZATION PROCESSING CONDITIONS EMPLOYING 7-TUBE FLUID BED - CONTINUOUS

| Run Number | Starch Moisture, % | Air Type | HCl, % d.b. | Time, Minutes | Temp. °C |
|---|---|---|---|---|---|
| 1 | 10.5 | Dry | 0.09 | 5 | 135–140.6 |
| 2 | 10.5 | Dry | 0.09 | 5 | 135–140.6 |
| 3 | 10.5 | Dry | 0.09 | 5 | 135–140.6 |
| 4 | 11.5 | Dry | 0.09 | 6 | 148.9 |

TABLE XVII-continued

DEXTRINIZATION PROCESSING CONDITIONS EMPLOYING 7-TUBE FLUID BED - CONTINUOUS

| Run Number | Starch Moisture, % | Air Type | HCl, % d.b. | Time, Minutes | Temp. °C |
|---|---|---|---|---|---|
| 5 | 11.5 | Dry | 0.09 | 6 | 148.9 |
| 6 | 11.5 | Dry | 0.09 | 6 | 148.9 |
| 7 | 12.0 | Dry | 0.09 | 6 | 143.3–154.4 |
| 8 | 11.9 | Dry | 0.09 | 6 | 143.3 |
| 9 | 10.9 | Dry | 0.09 | 6 | 146.1 |

The dextrin products prepared in the continuous 7-tube fluid bed were analyzed and characterized in the same manner as those produced in Examples 5(a) and 6(a). The product analysis and characteristics of the dextrins produced are set forth in Table XVIII, which follows.

b. Enzymatic Hydrolysis of Starch Dextrins

The starch dextrins prepared by the continuous dextrinization of starch in the 7-tube fluid bed were treated with bacterial alpha-amylase in the same manner as described in Example 5(b). The relative amounts of enzyme and product characterization are provided in Tables XIX, XX and XXI, as follows.

TABLE XVIII

PRODUCT ANALYSIS OF DEXTRINS PRODUCED FROM 7-TUBE FLUID BED - CONTINUOUS

| Run Number | D.E. | Moisture, % | Solubles, % d.b. | pH | FAV meq/g d.s. | Branching, % | IAV | DMSO Color, Calc. 40°Be | Viscosity, cp R.T. | Viscosity, cp 83°C |
|---|---|---|---|---|---|---|---|---|---|---|
| 1 | 5.0 | 3.6 | 86.6 | 2.6 | 1.18 | 7.6 | 0.56 | 19 | 150 | 20 |
| 2 | 5.1 | 3.1 | 91.0 | 2.5 | 1.20 | 7.7 | 0.50 | 29 | 75 | 17 |
| 3 | 5.0 | 3.5 | 91.2 | 2.6 | 1.22 | 8.3 | 0.56 | 26 | 85 | 19 |
| 4 | 5.8 | 3.1 | 89.8 | 2.5 | 1.37 | 8.9 | 0.50 | 22 | 120 | 16 |
| 5 | 5.3 | 2.5 | 91.5 | 2.5 | 1.39 | 10.4 | 0.44 | 30 | 80 | 14 |
| 6 | 4.9 | 2.4 | 93.2 | 2.7 | 1.38 | 11.2 | 0.40 | 38 | 90 | 17 |
| 7 | 4.8 | 2.4 | 95.3 | 2.6 | 1.51 | 14.2 | 0.36 | 120 | 45 | 10 |
| 8 | 3.7 | 2.4 | 94.9 | 2.6 | 1.28 | 12.4 | 0.38 | 43 | 38 | 27 |
| 9 | 4.1 | 1.8 | 95.5 | 2.7 | 1.40 | 13.5 | 0.35 | 86 | 29 | 14 |

TABLE XIX

LOW D.E. SYRUPS FROM DEXTRINS PRODUCED FROM 7-TUBE FLUID BED - CONTINUOUS

| Dextrin Run Number | Ht-1000, % d.b. | D.E. Dextrin | D.E. Syrup | Color (40°Be) | Filtration Rate | Clarity Stability, Days | IAV |
|---|---|---|---|---|---|---|---|
| 1 | 0.005 | 5.0 | 12.4 | 3.7 | n.d. | 12 | 0.49 |
| 2 | 0.005 | 5.1 | 11.9 | 8.4 | n.d. | 30 | 0.44 |
| 3 | 0.005 | 5.0 | 11.9 | 6.1 | n.d. | 12 | 0.53 |
| 4 | 0.005 | 5.8 | 12.6 | 4.6 | n.d. | 30 | 0.39 |
| 5 | 0.0055 | 5.3 | 12.1 | 7.1 | n.d. | 90 | 0.30 |
| 6 | 0.004 | 4.9 | 9.5 | 15.7 | 255 ml. | 36 | n.d. |
| 6A | 0.006 | 4.9 | 11.5 | 15.0 | 295 ml. | 90 | 0.12 |
| 6B | 0.008 | 4.9 | 12.1 | 14.6 | 355 ml. | 90 | n.d. |

TABLE XX

LOW D.E. SYRUPS FROM DEXTRINS PRODUCED FROM 7-TUBE FLUID BED - CONTINUOUS

| Dextrin Run Number | HT-1000, % d.b. | D.E. Dextrin | D.E. Syrup | Color, 40°Be | Filtration Rate | Clarity Stability, Days | Dextrin Branching, % | IAV Dextrin | IAV Syrup |
|---|---|---|---|---|---|---|---|---|---|
| 1 | 0.009 | 5.0 | 15.9 | 6.3 | 260 ml. | >90 | 7.6 | 0.56 | 0.12 |
| 2 | 0.009 | 5.1 | 14.7 | 11.7 | 320 ml. | >90 | 7.7 | 0.50 | 0.12 |
| 3 | 0.009 | 5.0 | 15.2 | 8.2 | 320 ml. | >90 | 8.3 | 0.56 | 0.16 |
| 4A | 0.009 | 5.8 | 15.2 | 6.4 | 315 ml. | >90 | 8.9 | 0.50 | — |
| 4B | 0.010 | 5.3 | 14.2 | 9.8 | 380 ml. | >90 | 10.4 | 0.44 | — |

TABLE XXI

LOW D.E. SYRUPS FROM DEXTRINS PRODUCED FROM 7-TUBE FLUID BED - CONTINUOUS

| Dextrin Run Number | HT-1000, % d.b. | D.E. Dextrin | D.E. Syrup | Color (40°Be) | Filtration Rate | Clarity Stability, Days | IAV |
|---|---|---|---|---|---|---|---|
| 7A | 0.002 | 4.8 | 6.5 | n.d. | n.d. | 2 | n.d. |
| 7B | 0.004 | 4.8 | 9.6 | n.d. | 350 ml. | >90 | n.d. |
| 7C | 0.006 | 4.8 | 10.9 | 57 | 385 ml. | >90 | n.d. |
| 7D | 0.008 | 4.8 | 11.7 | n.d. | n.d. | >90 | n.d. |
| 7E | 0.006[a] | 4.8 | 8.5 | n.d. | 265 ml. | 32 | n.d. |
| 7F | 0.015[b] | 4.8 | 9.5 | 39 | 450 ml. | >90 | n.d. |
| 7G | 0.025[b] | 4.8 | 10.7 | 35 | n.d. | >90 | n.d. |
| 8 | 0.025[b] | 3.7 | 12.1 | 13.0 | 350 ml. | >90 | 0.11 |
| 9 | 0.025[b] | 4.1 | 11.3 | 36.8 | 350 ml. | >90 | 0.05 |

[a]Only 50 ppm d.b. calcium added.
[b]Three to four hour enzymatic conversion.

The starch hydrolysate of Dextrin Run Number 7G was further refined by the procedure described in Example 5. This procedure is also outlined in the flow diagram set forth herein. More specifically, the hydrolysate from Dextrin Run Number 7G was first filtered at 60°C, followed by carbon treatment at 60°C for 30 minutes. The carbon treatment consisted of treating the crude hydrolysate with 2% Darco S-51 at a pH of 4.3. Following carbon treatment, the hydrolysate was evaporated to 30° Be. The concentrated syrup was then subjected to a two-stage ion exchange treatment. The first stage consisted of a cation exchange treatment with Duolite C-3 followed by the second stage, i.e, anion exchange treatment with Amberlite IRA-93 (C/A: 3/2; Flow rate = 2 B.V./hr.). Following the treatment with the ion exchange resins, the syrup was treated again with 2% Darco S-51 activated carbon at a pH of 4.3 at 60°C for 30 minutes. The refined hydrolysate syrup was thereafter further evaporated to about 70% solids, dry basis (38.6° Be). The syrup had a pH of about 4.2. The syrup remained haze-free at 70% solids for more than a year.

It can be seen from the above data that the remarkable results obtained here are dependent upon the combined steps of dextrinization to yield a dextrin product having the required percent of branching, and the subsequent step of enzymatic hydrolysis utilizing a bacterial alpha-amylase enzyme preparation.

Characterization Of The Hydrolysates Prepared In Examples 5, 6 and 7

The data provided in the tables of Examples 5, 6 and 7 illustrate that clarity stability of the syrup is directly related to branching in the starting starch dextrin. When the branching is less than 7%, the syrups of a 10–12 D.E. starch hydrolysate haze in less than 3 days. Increasing the branching to 7–10% by more rigorous dextrinization provides dextrins which give 10–12 D.E. syrups that remain clear for 7–30 days. Dextrins exhibiting greater than 10% branching provide 10–12 D.E. syrups that remain clear for over 90 days. In fact, most of the syrups characterized in Tables XIV, XIX, XX and XXI designated as stable for over 90 days have remained clear after a year's storage at room temperature at 70% solids. Some of these low D.E. syrups have remained clear for more than three years.

The data provided in the tables of Examples 5, 6 and 7 also indicate that the degree of branching of the starch dextrin to prepare a 14–16 D.E. syrup can be reduced to 7% to provide syrups which are resistant to haze formation. Thus, there is a correlation between the degree of branching in the starch dextrin and the final D.E. of the syrup to obtain the desired syrup clarity.

The data obtained from Examples 5, 6 and 7 further establish that the iodine absorbancy value is an excellent criterion for defining a dextrin that will yield a stable syrup. It was observed that acidification is not a critical step, since essentially the same IAV is obtained when the pH value is varied over the range of 2 to 8. It was observed that there is a definite progressive drop in IAV during the course of dextrinization. Wavelength of maximum absorption for the dextrins varied from about 545 to 556 nm. However, for each sample, the absorption peak is so broad that within experimental error absorbancy at 550 nm. is the same as that at λ maximum. Hence, the IAV data presented in the tables were determined using a single wavelength of 550 nm.

A direct relationship was found between dextrin IAV and syrup clarity stability. A similar direct relationship exists between syrup IAV and clarity stability. Thus, it is evident that finished syrup resistance to haze formation is obtained when one of the following requirements is met:

| 10–12 D.E. Syrup = | Dextrin IAV is 0.45 or less, Syrup IAV is 0.30 or less. |
| 14–16 D.E. Syrup = | Dextrin IAV is 0.70 or less, Syrup IAV is 0.22 or less. |

It should be noted that the IAV for dextrin is determined at 550 nm.–0.04 mg./ml., whereas the IAV for syrup prepared from the dextrin is determined at 500 nm.–1.00 mg./ml. Syrup clarity stability can be obtained at a minimum D.E. level of only 15 by enzymatically hydrolyzing a liquefied waxy starch by the process of Belgian Pat. No. 708,104. Such syrup has an IAV of 0.30, the same value required to obtain a stable 10–12 D.E. syrup from corn dextrin.

It can be seen from the above that iodine absorbancy value (IAV) is a reliable criterion for defining suitability of a dextrin for making a stable low D.E. syrup. The method for measuring IAV is simpler and more rapid than that used to measure FAV. IAV is also an excellent criterion for predicting syrup clarity stability or for monitoring enzymatic hydrolysis. In regard to the latter, experiments have been run which show that the IAV of a clarified hydrolysate, before or after carbon refining, is essentially the same as for finished syrups prepared from the hydrolysates.

A third criterion for establishing syrup clarity is the unique carbohydrate composition possessed by the syrups of the present invention. Paper chromatography analysis of the refined syrups characterized in Table XIV (Samples 1A and 3A) indicates that the $DP_1$–$DP_6$ of the dextrin hydrolysates have essentially the same carbohydrate distribution as the prior art low D.E. starch hydrolysates described in Belgian Pat. No. 708,104 and German Pat. No. 1,955,392. The carbohydrate composition of the dextrin hydrolysates of the present invention of $DP_1$–$DP_6$ is also essentially the same as the commercially available low D.E. starch hydrolysates, i.e., Mor-Rex Code 1918, manufactured and sold by CPC International Inc. and Maltrin, manufactured and sold by Grain Processing Corporation. Thus, the dextrin hydrolysates of the present invention, like the low D.E. hydrolysates of the prior art, have a descriptive ratio of at least about 2.

Several of the dextrin hydrolysates have been analyzed by gel permeation chromatography to ascertain their carbohydrate compositions in the $DP_{7+}$ region. Similar analyses were also conducted with the prior art low D.E. starch hydrolysates. The results of some of the data is set forth in Table XXII. In Table XXII, Samples 1 and 2 represent GPC analysis of the syrups of Example 5, Dextrin Run Numbers 21 and 23, respectively (Table X). Sample 3 is a low D.E. waxy starch hydrolysate, Mor-Rex Code 1918, produced by the enzymatic conversion of an enzyme liquefied waxy starch. Sample 4 is a low D.E. starch hydrolysate prepared by the enzymatic conversion of a liquefied corn starch.

TABLE XXII

CARBOHYDRATE DISTRIBUTION IN LOW D.E. PRODUCTS BY GEL PERMEATION CHROMATOGRAPHY

|  | Low D.E. Syrups From Dextrins | | Low D.E. Syrups From Liquefied Starch | |
|---|---|---|---|---|
|  | Sample 1[a] | Sample 2[b] | Sample 3[c] | Sample 4[d] |
| D.E. | 12.2 | 13.0 | 10.7 | 11.9 |
| Fraction, D.P. |  | Carbohydrate, % d.b. | | |
| A, 1 | 1.0 | 6.2 | 1.1 | 1.1 |
| B, 2 | 2.7 | 9.9 | 2.6 | 2.7 |
| C, 3–5 | 12.2 | 24.7 | 9.8 | 10.9 |
| D, 6–8 | 13.5 | 8.9 | 10.4 | 11.4 |
| E, 9–15 | 14.7 | 10.1 | 10.7 | 12.3 |
| F, 15–30 | 14.2 | 11.8 | 8.1 | 8.5 |
| G, 30–60 | 2.3 | 9.4 | 6.6 | 5.0 |
| H, 60–100 | 7.9 | 5.2 | 5.9 | 3.8 |
| I, 100–200 | 8.8 | 5.2 | 8.7 | 5.2 |
| J, 200+ | 12.3 | 8.2 | 35.4 | 38.5 |
| $\overline{M}w$ | 12,400 | 8,332 | 80,000 | 117,000 |
| $\overline{M}n$ | 1,400 | 704 | 1,760 | 1,660 |
| $\overline{M}w/\overline{M}n$ | 8.6 | 12 | 45 | 70 |

[a]Example 5, Dextrin Run Number 21.
[b]Example 5, Dextrin Run Number 23.
[c]Mor-Rex Code 1918.
[d]Mor-Rex Code 1910.

It is clearly evident from the data in Table XXII and other similar analyses that the dextrin derived syrups of the present invention have much lower weight average molecular weights than the prior art low D.E. products from unmodified but liquefied starches. It is also apparent that the dextrin derived syrups have a molecular weight distribution range which is much more narrow than the prior art low D.E. starch hydrolysates, as reflected by the polydispersity factors (i.e., $\overline{M}w/\overline{M}n$). The dextrin syrups of the present invention, as can be seen from the above data, also have a $DP_{200+}$ fraction (i.e., they contain less than 20%, by weight, dry basis, of starch oligosaccharides having a degree of polymerization greater than 200) which is less than those of the prior art hydrolysates. It appears as though hazing may not be solely a function of the $DP_{200+}$ fraction, but may also be influenced by a shift in carbohydrate distribution. In any event, the carbohydrate composition in the $DP_{7+}$ region of the syrups of the present invention is far different than the low D.E. syrup prepared by the enzymatic conversion of liquefied unmodified starches.

The starch hydrolysates of the invention are also characterized as being less viscous than conventional prior art products at comparable D.E. and solids levels. The viscosity difference is attributed to a reduction in the $DP_{200+}$ fraction and to a more narrow molecular weight distribution range as discussed hereinabove. Reduced viscosity is a definite advantage from a handling and economic viewpoint and in certain cases, from an applications viewpoint.

It was found that the filtration rates of the crude syrups of the invention could be improved by centrifugation. High speed centrifugation (30,000 × gravity) for 10 minutes at room temperature gives a three-phase system. The top layer contains most of the fat and protein, the middle layer is a clear liquor and the bottom layer contains undissolved starchy material. Continuous high speed centrifugation, however, in a sharpless centrifuge gives a two-phase system; a cloudy discharge, colloidal in nature, containing sugar liquor, fat and some protein and a dark brown deposit in the bowl. The middle phase of the batch operation and the discharge from continuous operation filter much more rapidly than the original syrup.

The syrups of the present invention were observed for mold growth during room temperature storage at 70% solids. In almost all the syrups evaluated, there was no evidence of any mold formation when the syrups were stored in an unopened condition for 90 days. This result is unexpected, since the prior art low D.E. starch hydrolysates mold when stored at room temperature for long periods of time. Thus, the syrups of the present invention have the advantage of shelf-life over the prior art hydrolysates.

In addition to the long shelf-life possessed by the syrups of the invention, the syrups of the invention have a taste advantage over the prior art syrups. The latter was established by a ten-member taste panel which evaluated samples of refined syrups of the invention. On a flavor basis, samples of the syrups of the present invention were preferred over the low D.E. starch hydrolysate, Mor-Rex Code 1918. The dextrin syrups of the present invention were noted for their blandness and extremely low sweetness.

As noted in the initial discussion here, the concentrated syrups may be subsequently put in the form of dry solids. In any event, the syrups or solids are characterized by blandness of taste and low sweetness, and they are non-hygroscopic. The syrups are haze-free, and when put in the form of solids, the solids when dissolved are fully and readily soluble in water. When used in food products, they have a minimal effect upon flavor, while providing bulk and stability.

The above characteristics make the products of the invention particularly suitable for applications such as, for example, as carriers for synthetic sweeteners, flavors, coloring agents and essences; spray-drying adjuncts for coffee extracts and tea extracts; bulking, bodying and dispersing agents in synthetic creams or as coffee whiteners; ingredients promoting moisture retention in breads, pastry and meat; and as components of dry soup mixes, bakery mixes, frosting mixes, spice mixes and blends, beverage powders, condiments, gravy mixes, and frozen dairy foods. In addition, they are useful in the formulation of anti-caking agents, tabletting compounds, whipped products, protective coatings, agglomeration aids, and low- or reduced-caloric foods and beverages.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

We claim:

1. A low D.E. starch hydrolysate having a D.E. in the range of from about 9 to about 20, a relatively narrow molecular weight distribution such that its weight average molecular weight to its number average molecular weight ratio of $\overline{M}w/\overline{M}n$ is less than about 20 and said hydrolysate being further characterized as containing less than about 20% by weight, dry basis, of starch oligosaccharides having a degree of polymerization greater than about 200.

2. The low D.E. starch hydrolysate of claim 1, wherein said ratio of $\overline{M}w/\overline{M}n$ is less than about 17.

3. The low D.E. starch hydrolysate of claim 1, wherein said ratio of $\overline{M}w/\overline{M}n$ is less than about 15.

4. The low D.E. starch hydrolysate of claim 1, wherein its ratio of $\overline{M}w/\overline{M}n$ is less than about 15 and said hydrolysate being further characterized as having less than about 15% by weight, dry basis, of starch oligosaccharides having a degree of polymerization greater than 200.

5. The low D.E. starch hydrolysate of claim 1, which is further characterized as having a descriptive ratio of at least about 2, said descriptive ratio being the quotient obtained by dividing the sum of the percentage of saccharides, dry basis, having a degree of polymerization of 1 to 6, by the D.E.

6. A low D.E. starch hydrolysate having a D.E. in the range of from about 9 to about 16, a relatively narrow molecular weight distribution such that its weight average molecular weight to its number average molecular weight ratio of $\overline{M}w/\overline{M}n$ is less than about 15 and being further characterized as having less than about 15% by weight, dry basis, of starch oligosaccharides having a degree of polymerization greater than about 200, said starch hydrolysate having a descriptive ratio of at least about 2, said descriptive ratio being the quotient obtained by dividing the sum of the percentage of saccharides, dry basis, having a degree of polymerization of 1 to 6, by the D.E.

7. A highly concentrated, non-brazing low D.E. syrup comprising a starch hydrolysate having a D.E. in the range of from about 9 to about 20, a relatively narrow molecular weight distribution such that its weight average molecular weight to its number average molecular weight of $\overline{M}w/\overline{M}n$ is less than about 20 and being further characterized as having less than about 20% by weight, dry basis, of starch oligosaccharides having a degree of polymerization greater than about 200, which when dissolved in water to a solids content of at least about 50% by weight, remains substantially haze-free over a relatively long period of time.

8. The syrup of claim 7, which has a solids content of about 65-75% by weight, dry basis.

9. The syrup of claim 7, wherein said starch hydrolysate is derived from corn starch.

10. The syrup of claim 7, wherein the D.E. is in the range of from about 9-16.

11. A process for producing a low D.E. starch hydrolysate of improved stability which comprises treating a starch dextrin having a degree of branching between about 7% and about 16% with a bacterial alpha-amylase enzyme at a temperature of from about 60°C to about 85°C to achieve a hydrolysate product having a D.E. in the range of from about 9 to about 20, whereby a stable, haze-free starch hydrolysate syrup is produced.

12. The process in accordance with claim 11, wherein said starch dextrin is prepared by subjecting starch in its natural dry state to the action of hydrochloric acid at a temperature in the range of from about 100°C to about 180°C.

13. A process for producing a low D.E. starch hydrolysate which comprises:
a. dextrinizing starch by introducing a bed of starch powder into a vessel, maintaining an upward flow of gas through said bed by introducing the gas from beneath said bed and withdrawing it from an outlet above the top of said bed, the upward velocity of said gas flow being sufficient to suspend and vigorously agitate the starch particles within said bed but insufficient to convey a substantial portion of the starch out through said upward outlet, heating said bed in said agitated condition to dextrinizing temperature and maintaining said dextrinizing temperature to provide a starch dextrin having a degree of branching of at least about 7%,
b. cooling said bed of agitated starch and withdrawing said starch dextrin from said vessel,
c. subjecting a mixture of said starch dextrin and water at a solids content less than about 50% by weight, dry basis, to the hydrolytic action of bacterial alpha-amylase at a temperature of about 60°C to about 85°C and a pH of from about 6 to about 9 to achieve a hydrolysate product having a D.E. of from about 9 to about 20,
d. stopping the hydrolytic reaction, and
e. recovering the hydrolysate so produced.

14. The process in accordance with claim 13, wherein said bed of starch powder is acidified prior to introducing it into said vessel.

15. The process in accordance with claim 13, wherein the starch is heated to a dextrinizing temperature in the range of from about 65°C to about 210°C.

16. The process in accordance with claim 13, wherein said dextrinizing and hydrolytic reactions are continuous.

17. The process in accordance with claim 13, wherein said starch dextrin has a degree of branching in the range of from about 9% to about 12%.

18. The process in accordance with claim 13 wherein the conversion is carried out under conditions to produce a hydrolysate having a D.E. in the range of from about 9 to about 16.

* * * * *